US011778893B2

(12) United States Patent
Kaelblein et al.

(10) Patent No.: US 11,778,893 B2
(45) Date of Patent: *Oct. 3, 2023

(54) INDACENO DERIVATIVES AS ORGANIC SEMICONDUCTORS

(71) Applicants: Clap Co., Ltd., Seoul (KR); King Abdullah University of Science & Technology, Thuwal (SA)

(72) Inventors: Daniel Kaelblein, Ludwigshafen (DE); Pascal Hayoz, Basel (CH); Hu Chen, Thuwal (SA); Iain McCulloch, Eastleigh (GB)

(73) Assignees: CLAP CO., LTD., Seoul (KR); KING ABDULLAH UNIVERSITY OF SCIENCE & TECHNOLOGY, Thuwal (SA)

( * ) Notice: Subject to any disclaimer, the term of this patent is extended or adjusted under 35 U.S.C. 154(b) by 222 days.

This patent is subject to a terminal disclaimer.

(21) Appl. No.: 17/285,445

(22) PCT Filed: Oct. 10, 2019

(86) PCT No.: PCT/EP2019/077446
§ 371 (c)(1),
(2) Date: Apr. 14, 2021

(87) PCT Pub. No.: WO2020/078815
PCT Pub. Date: Apr. 23, 2020

(65) Prior Publication Data
US 2021/0384434 A1 Dec. 9, 2021

(30) Foreign Application Priority Data

Oct. 15, 2018 (EP) .................................. 8200400

(51) Int. Cl.
*H10K 85/10* (2023.01)
*C07D 495/22* (2006.01)
(Continued)

(52) U.S. Cl.
CPC ......... *H10K 85/113* (2023.02); *C07D 495/22* (2013.01); *C08G 61/126* (2013.01);
(Continued)

(58) Field of Classification Search
CPC ...... C08G 2261/3223; C08G 2261/126; C08G 2261/124; C08G 2261/95; C08G 2261/91;
(Continued)

(56) References Cited

U.S. PATENT DOCUMENTS

2005/0082525 A1* 4/2005 Heeney ................ C08G 61/126
257/40
2013/0320316 A1* 12/2013 Park .................... H01L 51/0074
257/40

FOREIGN PATENT DOCUMENTS

CN 102482291 5/2012
CN 104245786 1/2017
(Continued)

OTHER PUBLICATIONS

Cai et al., "Exceptional Single-Molecule Transport Properties of Ladder-Type Heteroacene Molecular Wires," J Am Chem Soc (2016) 138(33): 10630-10635.
(Continued)

*Primary Examiner* — Shane Fang
(74) *Attorney, Agent, or Firm* — NORTON ROSE FULBRIGHT US LLP

(57) ABSTRACT

The present invention provides compounds comprising at least one unit of formula (1) or (1') as well as a process for the preparation of the compounds, intermediates of this
(Continued)

Figure 1:
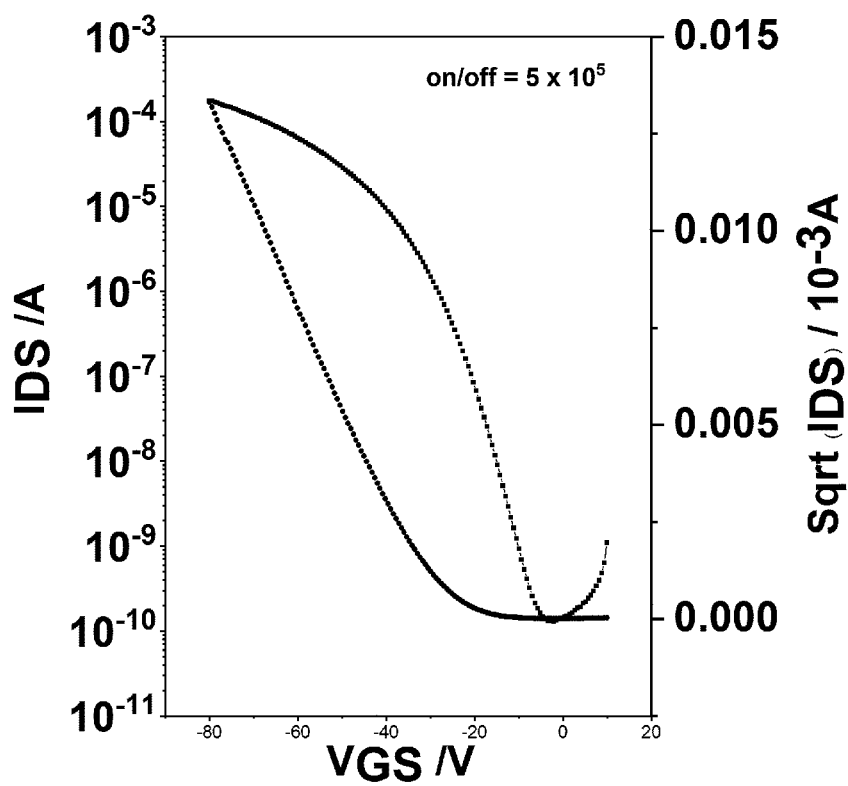

process, electronic devices comprising the compounds, and the use of the compounds as semiconducting materials.

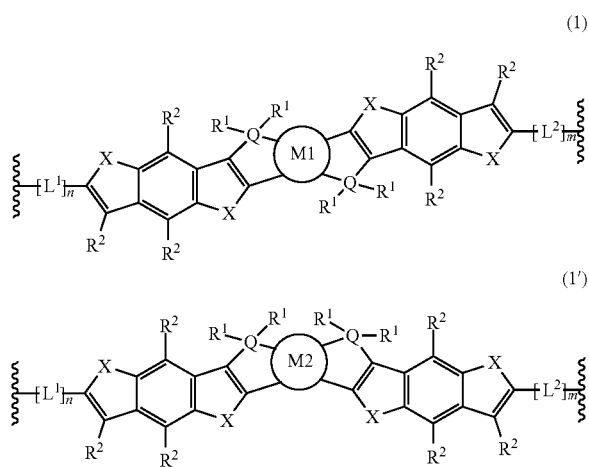

14 Claims, 2 Drawing Sheets

(51) Int. Cl.
C08G 61/12 (2006.01)
H10K 10/46 (2023.01)
(52) U.S. Cl.
CPC ..... H10K 85/151 (2023.02); *C08G 2261/124* (2013.01); *C08G 2261/1412* (2013.01); *C08G 2261/18* (2013.01); *C08G 2261/228* (2013.01); *C08G 2261/3243* (2013.01); *C08G 2261/3246* (2013.01); *C08G 2261/92* (2013.01); *H10K 10/464* (2023.02)

(58) Field of Classification Search
CPC ..... C07D 417/14; C07D 495/22; H01L 51/00; H01L 51/0074; H01L 51/0071; H01L 51/0072; H01L 51/0073; H01L 51/0558
See application file for complete search history.

(56) References Cited

FOREIGN PATENT DOCUMENTS

GB 2472413 A 2/2011
JP 2008-300752 12/2008
WO WO 2018/104367 6/2018

OTHER PUBLICATIONS

Cai et al., "Synthesis of Alternating Donor-Acceptor Ladder-Type Molecules and Investigation of Their Multiple Charge-Transfer Pathways," Angew Chem Int Ed Engl. (2018) 57(22): 6442-6448.
Zhang et al., "Indacenodithiophene semiconducting polymers for high-performance, air-stable transistors," J Am Chem Soc. (2010) 132(33): 11437-11439.
Zheng et al., "Roles of Quinoidal Character and Regioregularity in Determining the Optoelectronic and Photovoltaic Properties of Conjugated Copolymers," Macromolecules (2014) 47:18; 6252-6259.
Office Action issued in corresponding Chinese Application No. 201980068019.0, dated Feb. 13, 2023.

* cited by examiner

INDACENO DERIVATIVES AS ORGANIC SEMICONDUCTORS

CROSS REFERENCE TO RELATED APPLICATIONS

This application is a national stage application under 35 U.S.C. § 371 of International Application No. PCT/EP2019/077446, filed internationally on Oct. 10, 2019, which claims priority to and benefit of European Patent Application No. 18200400.2, filed in the European Patent Office on Oct. 15, 2018, the entire contents of which are incorporated herein by reference.

The present invention relates to compounds, including polymers, a process for the preparation of these compounds, to intermediates of the process, to electronic devices comprising these compounds, as well as to the use of these compounds as semiconducting material.

Organic semiconducting materials can be used in electronic devices such as organic photovoltaic devices (OPVs), organic field-effect transistors (OFETs), organic light emitting diodes (OLEDs), organic photodiodes (OPDs) and organic electrochromic devices (ECDs).

It is desirable that the organic semiconducting materials are compatible with liquid processing techniques such as spin coating as liquid processing techniques are convenient from the point of processability, and thus allow the production of low cost organic semiconducting material-based electronic devices. In addition, liquid processing techniques are also compatible with plastic substrates, and thus allow the production of light weight and mechanically flexible organic semiconducting material-based electronic devices.

For application in organic photovoltaic devices (OPVs), organic field-effect transistors (OFETs), and organic photodiodes (OPDs), it is further desirable that the organic semiconducting materials show high charge carrier mobility and are of high stability under ambient conditions.

It was the object of the present invention to provide new and improved organic semiconducting materials.

This object is solved by the compounds of claim 1, the process of claim 12, the intermediates of claim 13, the electronic device of claim 15 and the use of the compounds of claim 17.

The compounds of the present invention comprise at least one unit of formula

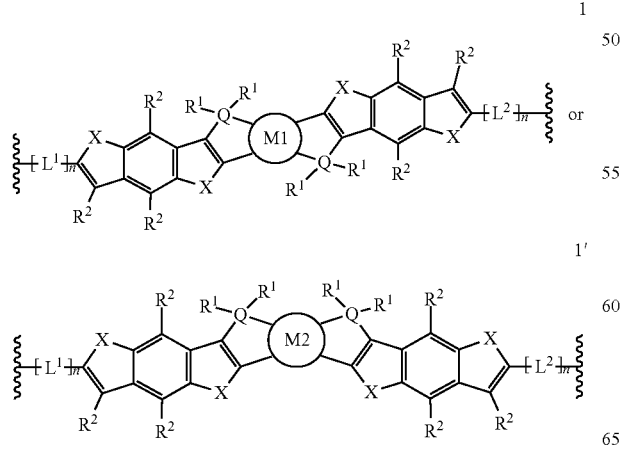

wherein
M1 and M2 are independently of each other an aromatic or heteroaromatic monocyclic or bicyclic ring system;
X is at each occurrence O, S, Se or Te,
Q is at each occurrence C, Si or Ge,
$R^1$ is at each occurrence selected from the group consisting of H, $C_{1-50}$-alkyl, $-[CH_2]_o-[OSiR^aR^a]_p-OSiR^a-R^aR^a$, $-[CH_2]_o-[R^aR^aSi-O]_p-SiR^aR^aR^a$, $-[CR^bR^b]_q-CR^bR^bR^b$, $C_{2-50}$-alkenyl, $C_{2-50}$-alkynyl, $C_{5-8}$-cycloalkyl, $C_{6-14}$-aryl and 5 to 14 membered heteroaryl,
wherein
is an integer from 0 to 10,
p is an integer from 1 to 40,
$R^a$ is at each occurrence $C_{1-10}$-alkyl, $C_{2-10}$-alkenyl or $C_{2-10}$-alkynyl,
q is an integer from 1 to 50,
$R^b$ is at each occurrence H or halogen, with the provisio that not all $R^b$ in $-[CR^bR^b]_q-CR^bR^bR^b$ are H,
$C_{1-50}$-alkyl, $C_{2-50}$-alkenyl and $C_{2-50}$-alkynyl can be substituted with one to four substituents independently selected from the group consisting of $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R^c]$, $SR^c$, CN, $-SiR^cR^cR^c$ and $NO_2$,
$C_{5-8}$-cycloalkyl can be substituted with one or two substituents independently selected from the group consisting of $C_{1-10}$-alkyl, $C_{2-10}$-alkenyl, $C_{2-10}$-alkynyl, $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R^c]$, $SR^c$, halogen, CN, $-SiR^cR^cR^c$ and $NO_2$; and one $CH_2$-group of $C_{5-8}$-cycloalkyl can be replaced by O, S, OC(O), CO, $NR^c$ or $NR^c-CO$,
$C_{6-14}$-aryl and 5 to 14 membered heteroaryl can be substituted with one to three substituents independently selected from the group consisting of $C_{1-10}$-alkyl, $C_{2-10}$-alkenyl, $C_{2-10}$-alkynyl, $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R^c]$, $SR^c$, halogen, CN, and $NO_2$,
wherein
$R^c$ is at each occurrence H, $C_{1-20}$-alkyl, $C_{2-10}$-alkenyl or $C_{2-10}$-alkynyl,
$R^2$ is at each occurrence H, $C_{1-30}$-alkyl, $C_{2-30}$-alkenyl or $C_{2-30}$-alkynyl or halogen,
n is 0, 1, 2, 3 or 4,
m is 0, 1, 2, 3 or 4,
$L^1$ and $L^2$ are independently from each other and at each occurrence selected from the group consisting of $C_{6-26}$-arylene, 5 to 20 membered heteroarylene,

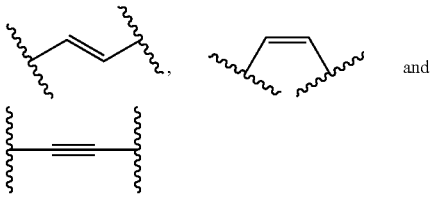

wherein
$C_{6-26}$-arylene and 5 to 20 membered heteroarylene can be substituted with one to four substituents $R^d$ at each occurrence selected from the group consisting of H, $C_{1-30}$-alkyl, $C_{2-30}$-alkenyl, $C_{2-30}$-alkynyl and halogen, and

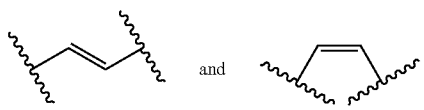 and can be substituted with one or two substituents at each occurrence selected from the group consisting of $R^e$, $COOR^e$ and CN, wherein $R^e$ is at each occurrence selected from the group consisting of H, $C_{1-30}$-alkyl, $C_{2-30}$-alkenyl and $C_{2-30}$-alkynyl.

$C_{1-10}$-alkyl, $C_{1-20}$-alkyl, $C_{1-30}$-alkyl and $C_{1-50}$-alkyl can be branched or unbranched. Examples of $C_{1-10}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl, n-(2-ethyl)hexyl, n-nonyl and n-decyl. Examples of $C_{1-20}$-alkyl are $C_{1-10}$-alkyl and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl ($C_{20}$). Examples of $C_{1-30}$-alkyl and $C_{1-50}$-alkyl are $C_{1-20}$-alkyl and n-docosyl ($C_{22}$), n-tetracosyl ($C_{24}$), n-hexacosyl ($C_{26}$), n-octacosyl ($C_2$) and n-triacontyl ($C_{30}$).

$C_{2-10}$-alkenyl, $C_{2-20}$-alkenyl, $C_{2-30}$-alkenyl and $C_{2-50}$-alkenyl can be branched or unbranched. Examples of $C_{1-20}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of $C_{2-20}$-alkenyl are $C_{2-10}$-alkenyl and linoleyl ($C_{18}$), linolenyl ($C_{18}$), oleyl ($C_{18}$), and arachidonyl ($C_{20}$). Examples of $C_{2-50}$alkenyl are $C_{2-20}$-alkenyl and erucyl ($C_{22}$).

$C_{2-10}$-alkynyl, $C_{2-20}$-alkynyl and $C_{2-50}$-alkynyl can be branched or unbranched. Examples of $C_{2-10}$-alkynyl are ethynyl, 2-propynyl, 2-butynyl, 3-butynyl, pentynyl, hexynyl, heptynyl, octynyl, nonynyl and decynyl. Examples of $C_{2-20}$-alkynyl and $C_{2-50}$alkynyl are undecynyl, dodecynyl, undecynyl, dodecynyl, tridecynyl, tetradecynyl, pentadecynyl, hexadecynyl, heptadecynyl, octadecynyl, nonadecynyl and icosynyl ($C_{20}$).

Examples of $C_{5-8}$-cycloalkyl are cyclopentyl, cyclohexyl, cycloheptyl and cyclooctyl.

Halogen can be F, Cl, Br and I.

$C_{6-14}$-aryl is a 6 to 14 membered monocyclic or polycyclic, such as dicyclic, tricyclic, ring system, wherein the rings are either condensed to each other or connected via a double bond, which $C_{6-14}$-aryl comprises at least one C-aromatic ring, and which $C_{6-14}$-aryl may also comprise non-aromatic rings, which non-aromatic rings may comprise heteroatoms such as O, S, Se, Te, Si, N and Ge, and which C-aromatic rings or non-aromatic ring may be substituted, for example by $C_{1-30}$-alkyl, $=O$, $=C(C_{1-30}$-alkyl$)_2$ or $=C(CN)_2$.

Examples of $C_{6-14}$-aryl are

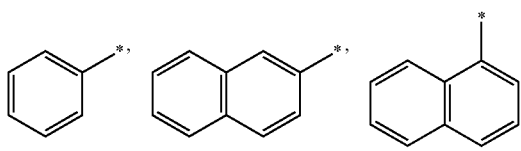

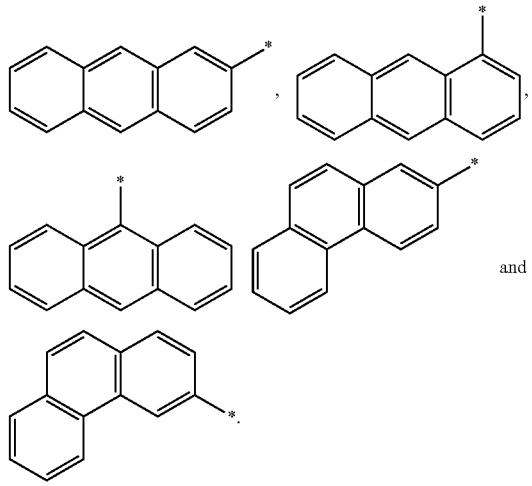

and 5 to 14 membered heteroaryl is a 5 to 14 membered monocyclic or polycyclic, such as dicyclic, tricyclic or tetracyclic, ring system, wherein the rings are either condensed to each other or connected via a double bond, which 5 to 14 membered heteroaryl comprises at least one heteroaromatic ring having at least one heteroatom selected from the group consisting of O, S, Se, N and Te, and which 5 to 14 membered heteroaryl may also comprise aromatic carbon rings or non-aromatic rings, which non-aromatic ring may comprise heteroatoms such as O, S, Se, Te, Si, N and Ge, and which heteroaromatic rings, aromatic carbon rings or non-aromatic rings may be substituted, for example by $C_{1-30}$-alkyl, $=O$, $=C(C_{1-30}$-alkyl$)_2$ or $=C(CN)_2$.

Examples of 5 to 14 membered heteroaryl are

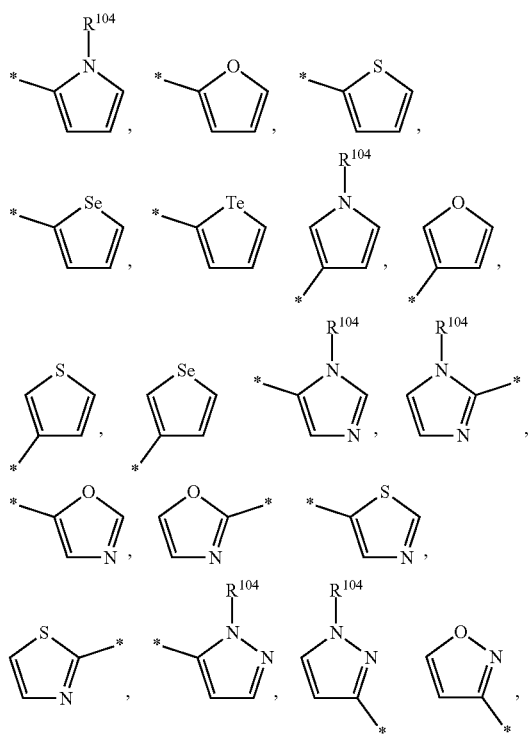

-continued
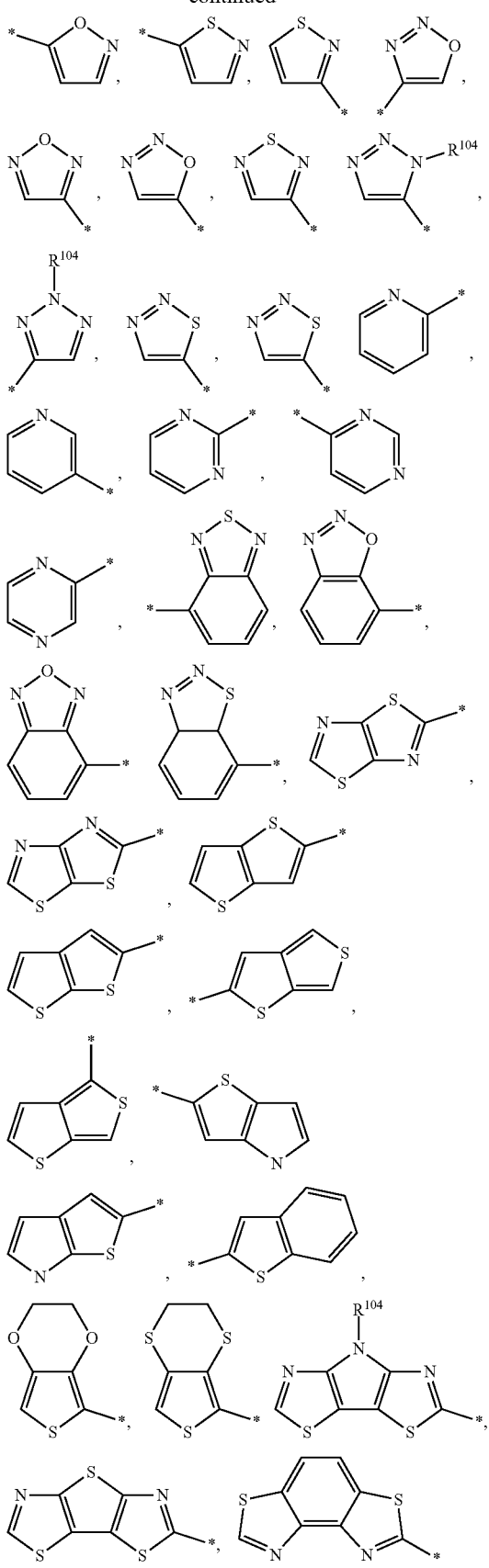
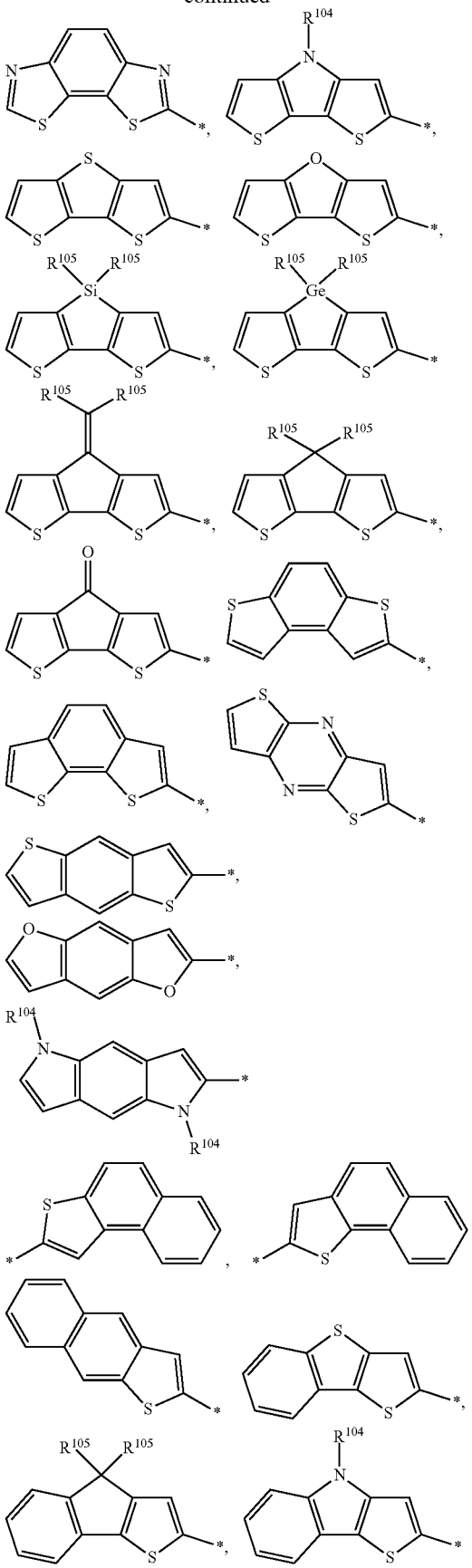

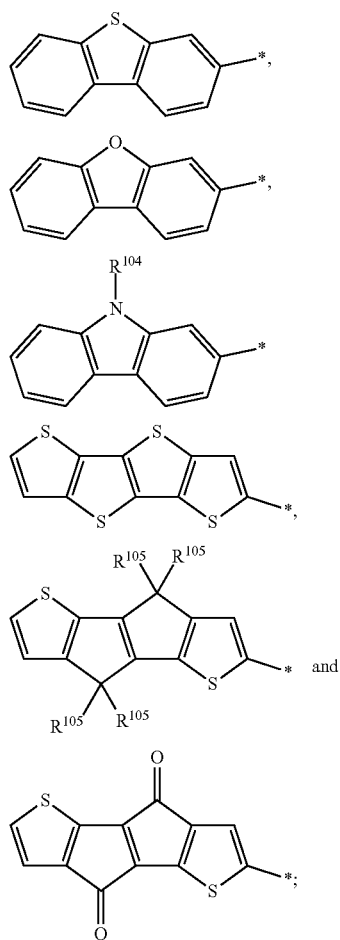

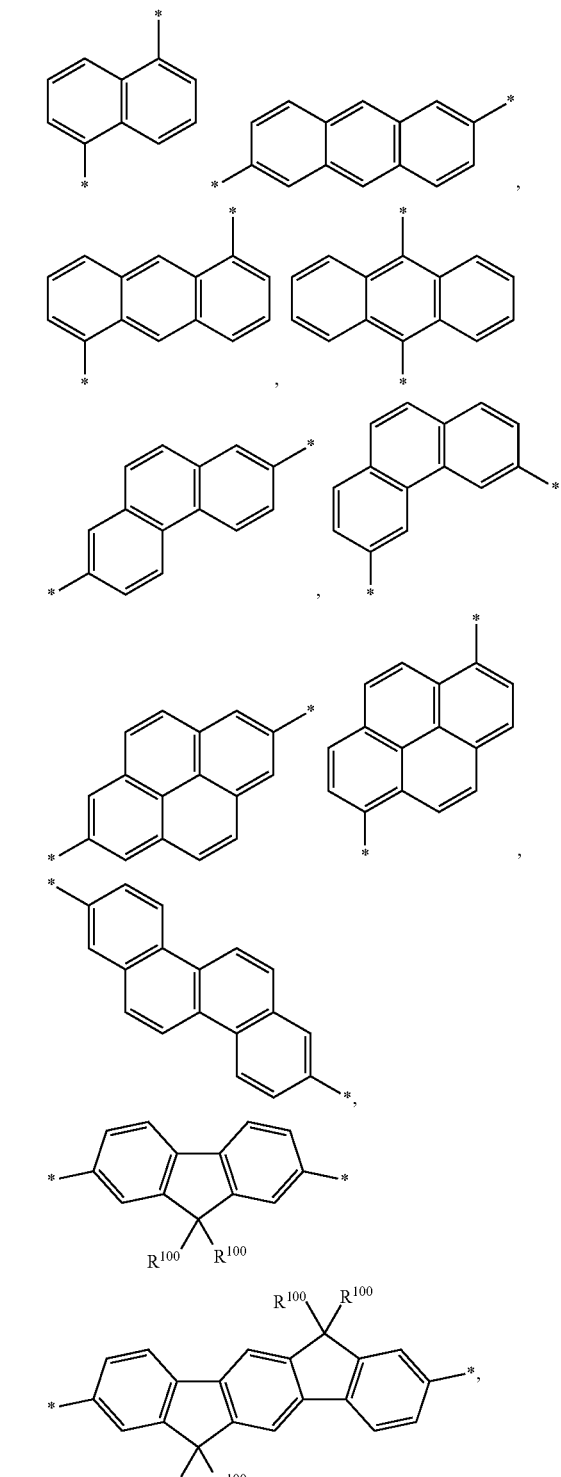

wherein $R^{105}$ is at each occurrence H, $C_{1-30}$-alkyl, $C_{2-30}$-alkenyl or $C_{2-30}$-alkynyl or halogen, $R^{104}$ is at each occurrence H or $C_{1-30}$-alkyl.

$C_{6-26}$-arylene is a 6 to 26 membered monocyclic or polycyclic, such as dicyclic, tricyclic, tetracyclic, pentacyclic or hexacyclic ring system, wherein the rings are either condensed to each other or connected via a double bond, which $C_{6-26}$-arylene comprises at least one C-aromatic ring, and which $C_{6-26}$-arylene may also comprise non-aromatic rings, which non-aromatic rings may comprise heteroatoms such as O, S, Se, Te, Si, N and Ge, and which C-aromatic rings or non-aromatic ring may be substituted, for example by $C_{1-30}$-alkyl, $=$O, $=C(C_{1-30}$-alkyl$)_2$ or $=C(CN)_2$.

Examples of $C_{6-26}$-arylene are

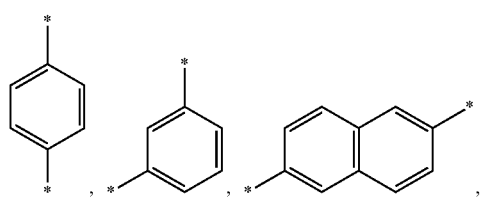

-continued

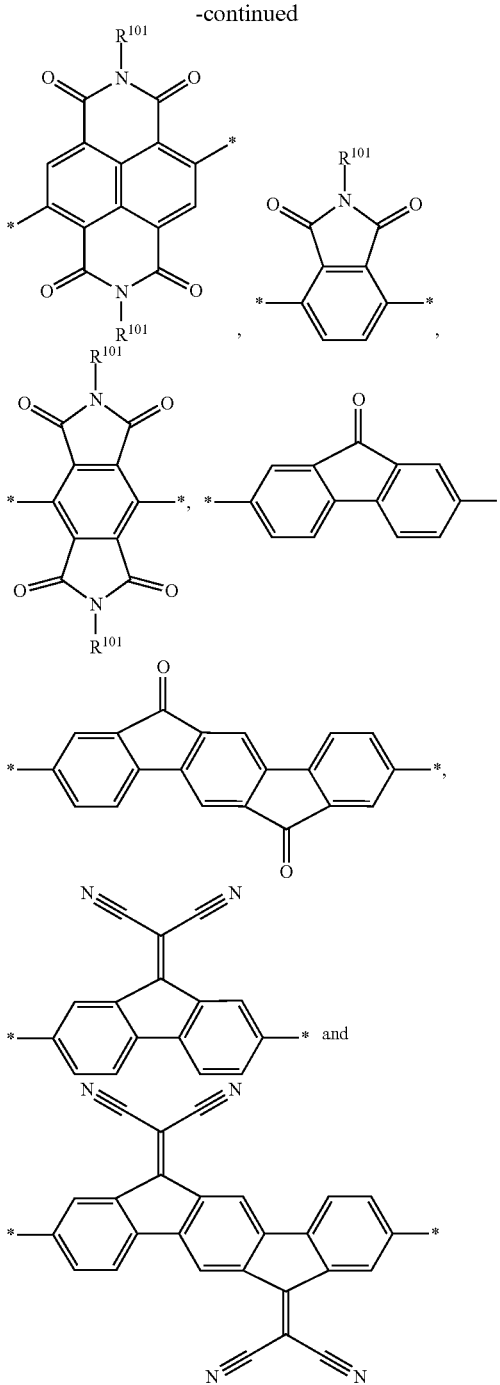

wherein
R$^{100}$ is at each occurrence H, C$_{1-30}$-alkyl, C$_{2-30}$-alkenyl or C$_{2-30}$-alkynyl or halogen,
R$^{101}$ is at each occurrence H or C$_{1-30}$-alkyl.
5 to 20 membered heteroarylene is a 5 to 20 membered monocyclic or polycyclic, such as dicyclic, tricyclic, tetracyclic, pentacyclic or hexacyclic ring system, wherein the rings are either condensed to each other or connected via a double bond, which 5 to 20 membered heteroarylene comprises at least one heteroaromatic ring having at least one heteroatom selected from the group consisting of O, S, Se, N and Te, and which 5 to 20 membered heteroarylene may also comprise aromatic carbon rings or non-aromatic rings, which non-aromatic ring may comprise heteroatoms such as O, S, Se, Te, Si, N and Ge, and which heteroaromatic rings, aromatic carbon rings or non-aromatic rings may be substituted, for example by C$_{1-30}$-alkyl, =O, =C(C$_{1-30}$-alkyl)$_2$ or =C(CN)$_2$.

Examples of 5 to 20 membered heteroarylene are

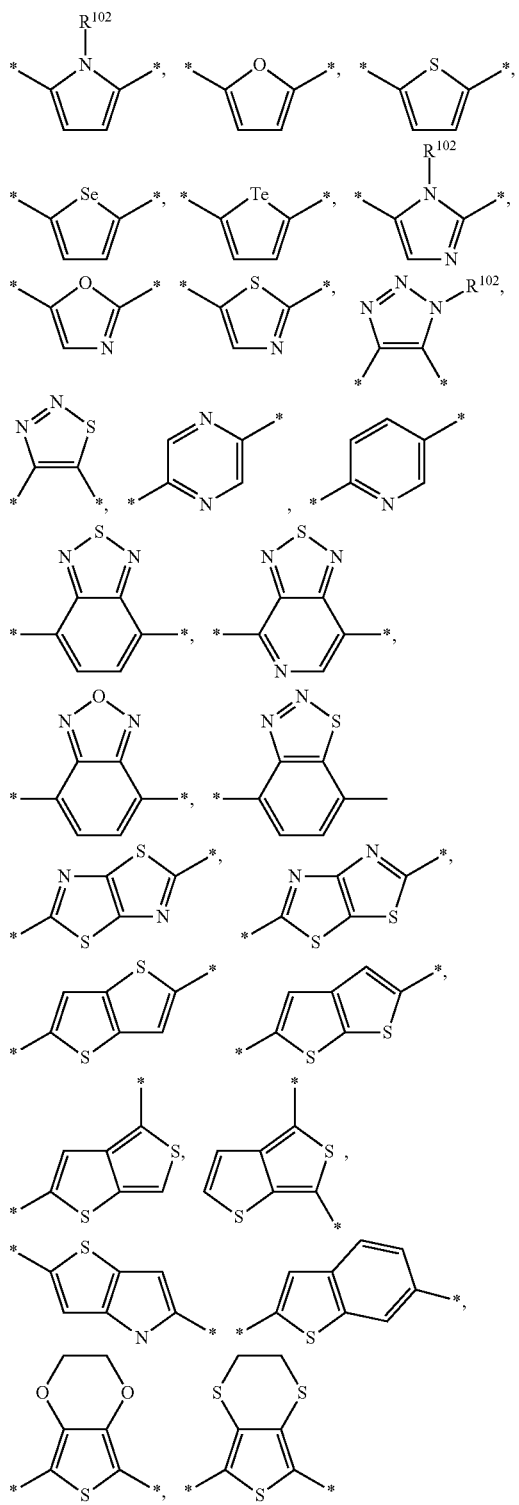

-continued
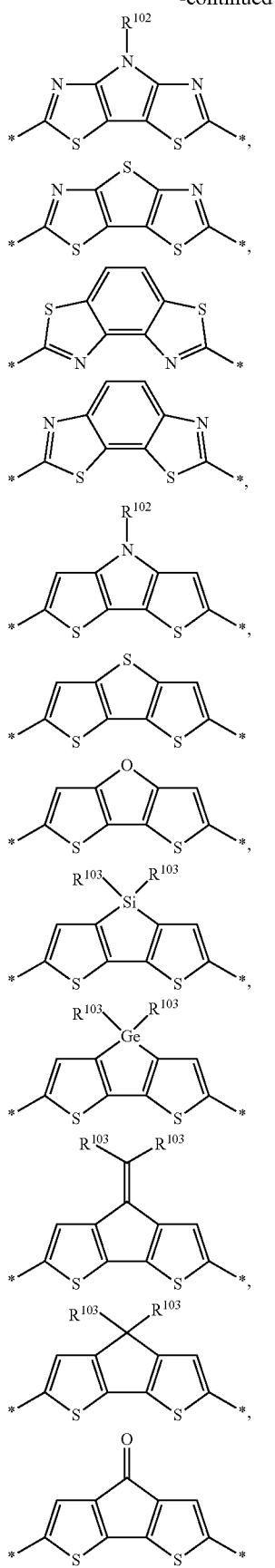
-continued
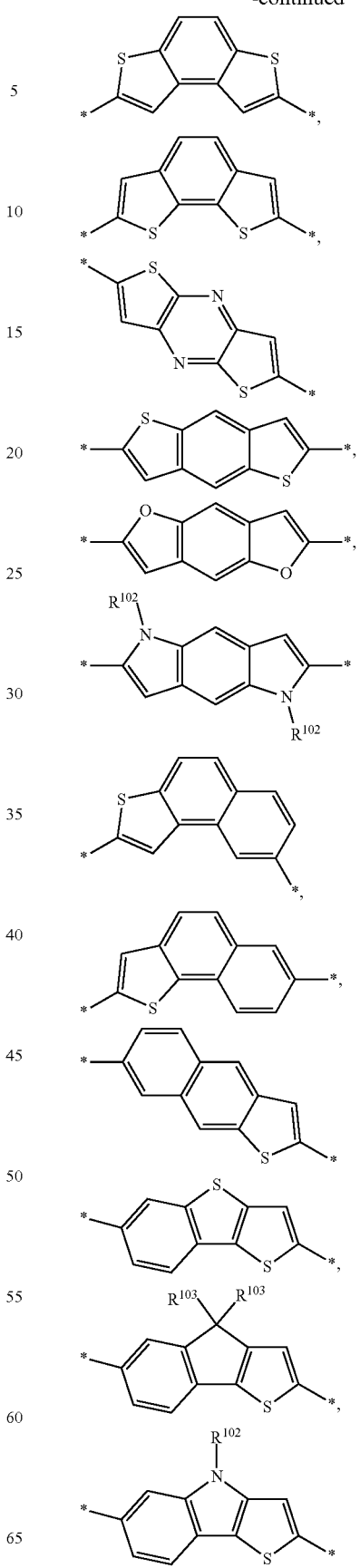

-continued
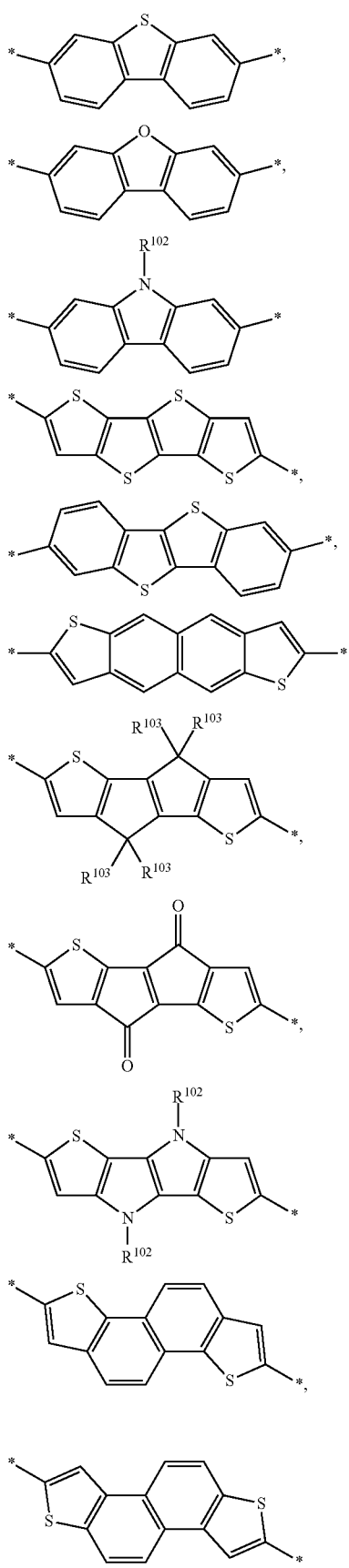
-continued
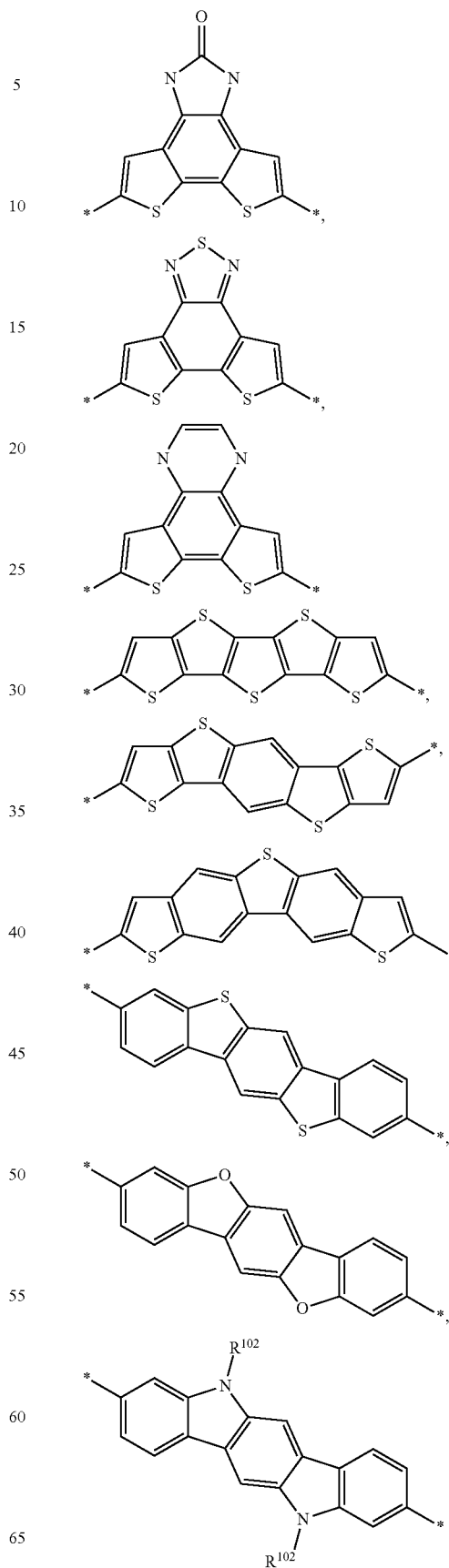

-continued
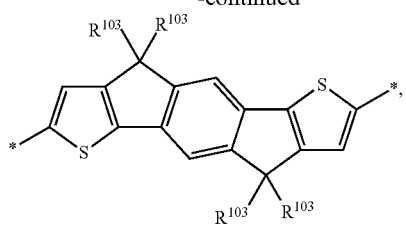
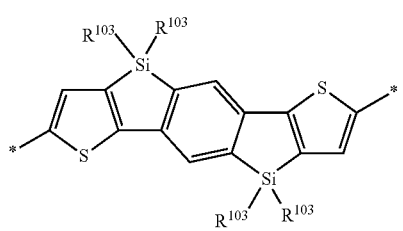
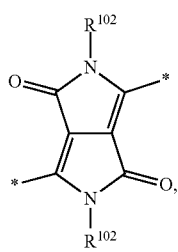 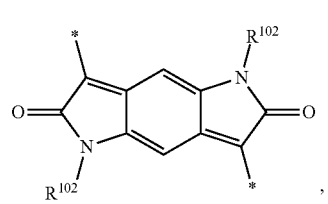
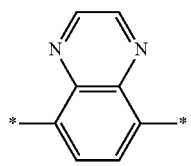 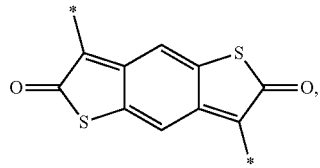
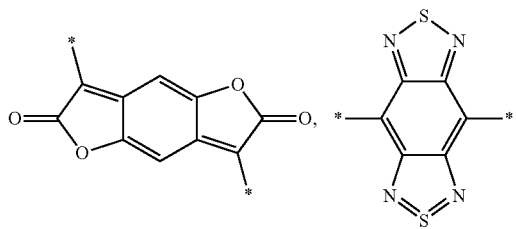
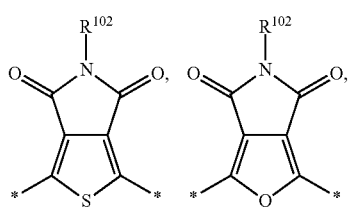
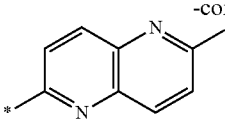
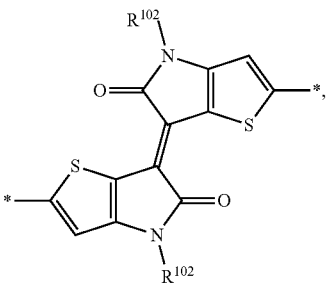
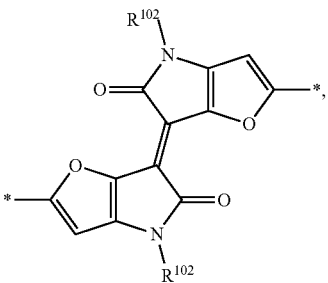
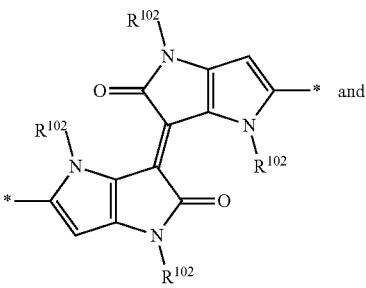 and
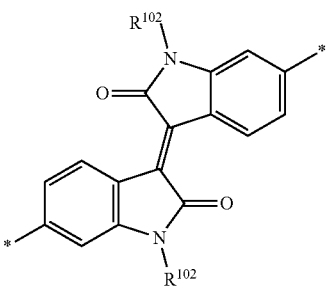
wherein
$R^{103}$ is at each occurrence H, $C_{1-30}$-alkyl, $C_{2-30}$-alkenyl or $C_{2-30}$-alkynyl or halogen,
$R^{102}$ is at each occurrence H or $C_{1-30}$-alkyl.

Preferred compounds of the present invention comprise at least one unit of formula
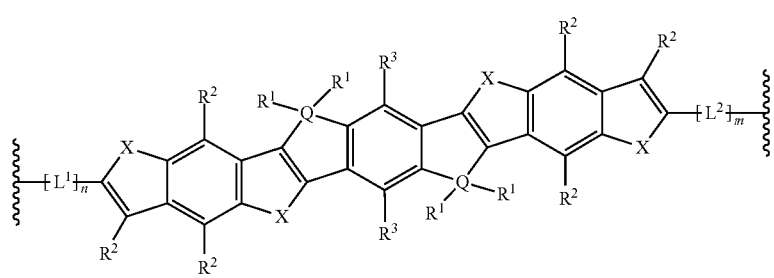
1A
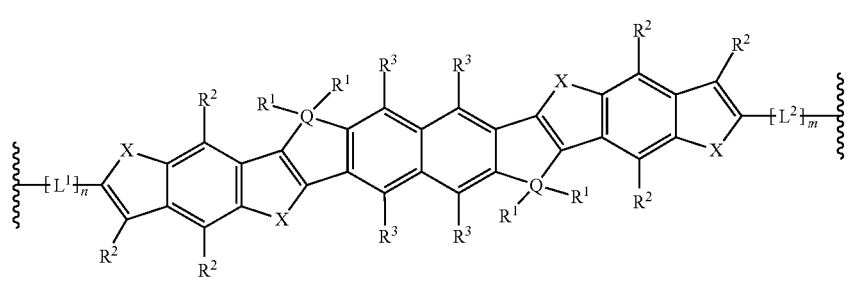
1B
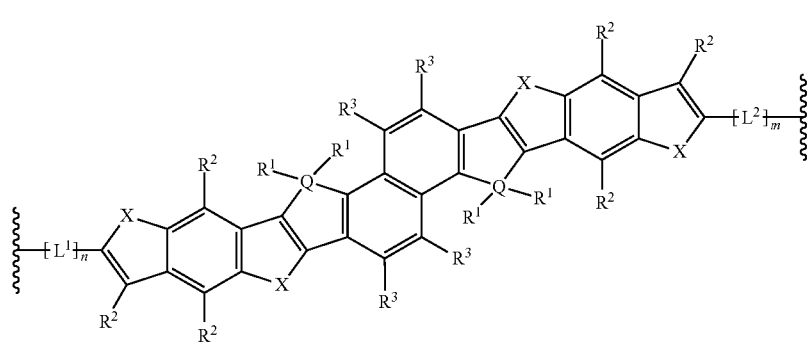
1C
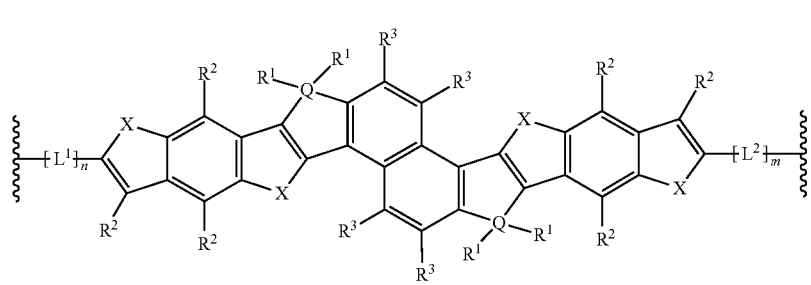
1D
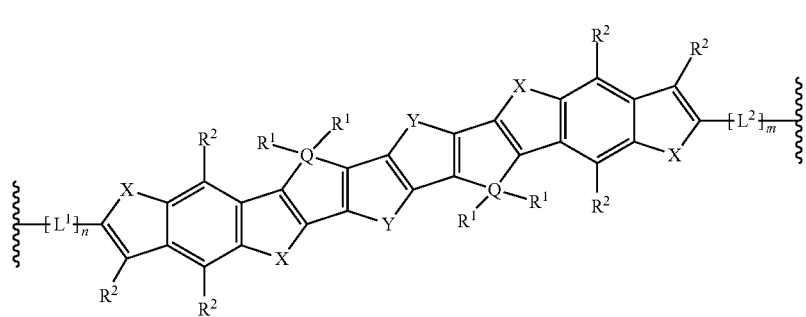
1E

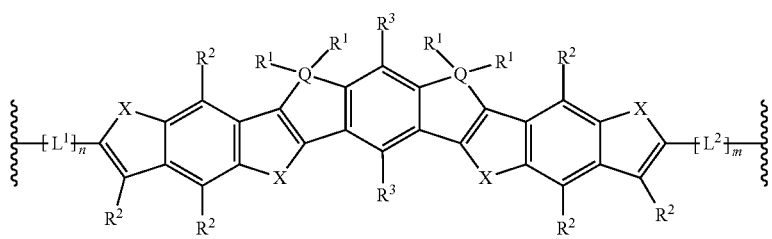

1'A

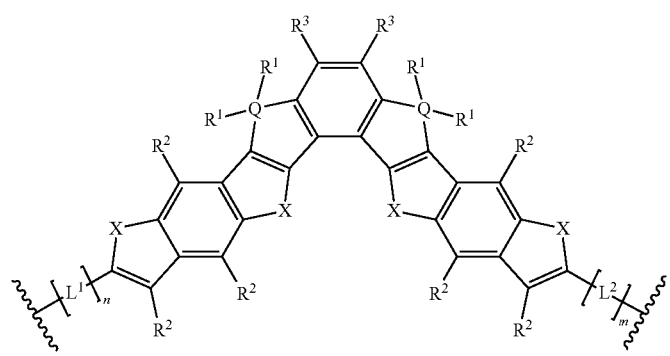

1'B

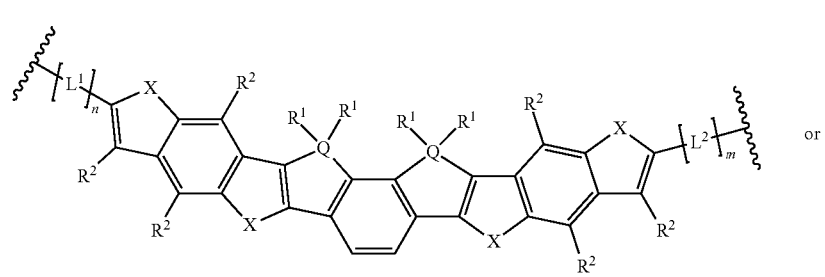

1'C or

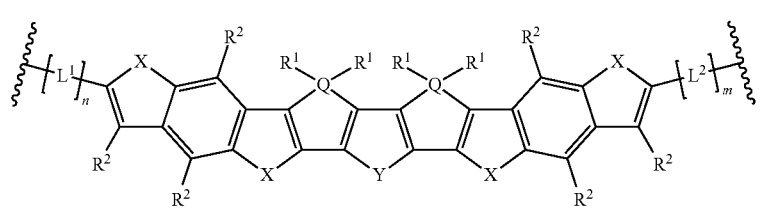

1'D wherein

X, Q, R$^1$, R$^2$, L$^1$, L$^2$, n and m are as defined above, and Y is at each occurrence O, S, Se or Te, and R$^3$ is at each occurrence H, C$_{1-30}$-alkyl, C$_{2-30}$-alkenyl or C$_{2-30}$-alkynyl or halogen.

More preferred compounds of the present invention comprise at least one unit of formula 1A, 1B, 1C or 1D.

Most preferred compounds of the present invention comprise at least one unit of formula 1A.

The compounds of the present invention can be small molecules or polymers.

The compounds of the present invention which are small molecules preferably comprise one or two units of formula 1 or 1' as defined above.

Small molecules have preferably a weight average molecular weight (M$_w$) of below 1 kDa, more preferably of below 800 Da, and a number average molecular weight (M$_n$) of below 1 kDa, more preferably of below 800 Da.

Preferably, the compounds of the present invention are polymers.

The compounds of the present invention which are polymers preferably comprise at least three units of formula 1 or 1' as defined above.

The polymers have preferably a weight average molecular weight (M$_w$) of 1 to 10000 kDa and a number average molecular weight (M$_n$) of 1 to 10000 kDa. The polymers of the present invention have more preferably a weight average molecular weight (M$_w$) of 1 to 1000 kDa and a number average molecular weight (M$_n$) of 1 to 100 kDa. The polymers of the present invention have even more preferably a weight average molecular weight (M$_w$) of 5 to 1000 kDa and a number average molecular weight (M$_n$) of 5 to 100 kDa. The polymers of the present invention have still more preferably a weight average molecular weight (M$_w$) of 10 to 1000 kDa and a number average molecular weight (M$_n$) of 10 to 100 kDa. The polymers of the present invention have most preferably a weight average molecular weight (M$_w$) of 10 to 100 kDa and a number average molecular weight (M$_n$) of 5 to 60 kDa. The weight average molecular weight (M$_w$) and the number average molecular weight (M$_n$) can be determined by gel permeation chromatography (GPC) e.g. at 80° C. using chlorobenzene or preferably at 150° C. using trichlorobenzene as eluent and a polystyrene as standard.

More preferably, the compounds of the present invention are polymers comprising at least 60% by weight of the units of formula 1 or 1' based on the weight of the polymer.

Even more preferably, the compounds of the present invention are polymers comprising at least 80% by weight of the units of formula 1 or 1' based on the weight of the polymer.

Most preferably, the compounds of the present invention are polymers comprising at least 95% by weight of the units of formula 1 or 1' based on the weight of the polymer.

Preferably, X is at each occurrence O, S or Se. More preferably, X is at each occurrence S or Se. Most preferably, X is at each occurrence S.

Preferably, Y is at each occurrence O, S or Se. More preferably, Y is at each occurrence S or Se. Most preferably, Y is at each occurrence S.

Preferably Q is at each occurrence C or Si. More preferably Q is at each occurrence C.

Preferably, $R^1$ is at each occurrence selected from the group consisting of H, $C_{1-50}$-alkyl, —[$CH_2$]$_o$—[$R^aR^aSi$—O]$_p$—$SiR^aR^aR^a$, —[$CR^bR^b$]$_q$—$CR^bR^bR^b$, $C_{2-50}$-alkenyl and $C_{2-50}$-alkynyl,
  wherein
  is an integer from 1 to 10,
  p is an integer from 1 to 40,
  $R^a$ is at each occurrence $C_{1-10}$-alkyl, $C_{2-10}$-alkenyl or $C_{2-10}$-alkynyl,
  q is an integer from 1 to 50,
  $R^b$ is at each occurrence H or halogen, with the proviso that not all $R^b$ in —[$CR^bR^b$]$_q$—$CR^bR^bR^b$ are H,
  $C_{1-50}$-alkyl, $C_{2-50}$-alkenyl and $C_{2-50}$-alkynyl can be substituted with one to four substituents independently selected from the group consisting of $OR^c$, $OC(O)$—$R^c$, $C(O)$—$OR^c$, $C(O)$—$R^c$, $NR^cR^c$, $NR^c$—$C(O)R^c$, $C(O)$—$NR^cR^c$, $N[C(O)R^c][C(O)R^c]$, $SR^c$, CN, and $NO_2$,
    wherein
    $R^c$ is at each occurrence H, $C_{1-20}$-alkyl, $C_{2-10}$-alkenyl or $C_{2-10}$-alkynyl.

More preferably, $R^1$ is at each occurrence $C_{1-50}$-alkyl. Most preferably, $R^1$ is at each occurrence $C_{6-30}$-alkyl.

Preferably, $R^2$ is at each occurrence H, $C_{1-30}$-alkyl or halogen. More preferably, $R^2$ is at each occurrence H.

Preferably, $R^3$ is at each occurrence H, $C_{1-30}$-alkyl or halogen. More preferably, $R^3$ is at each occurrence H.

Preferably, X, Q, $R^1$ and $R^2$ are at each occurrence the same. If Y and $R^3$ are present, Y and $R^3$ are preferably at each occurrence the same.

Preferably, n is 0, 1 or 2. More preferably, n is 0 or 1. Most preferably, n is 0.

Preferably, m is 0, 1, 2 or 3. More preferably, m is 0, 1 or 2. Most preferably, m is 1.

Preferably, $L^1$ and $L^2$ are independently from each other and at each occurrence selected from the group consisting of $C_{6-26}$-arylene, 5 to 20 membered heteroarylene, and

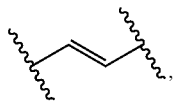

wherein $C_{6-26}$-arylene and 5 to 20 membered heteroarylene can be substituted with one to four substituents $R^d$ at each occurrence selected from the group consisting of $C_{1-30}$-alkyl, $C_{2-30}$-alkenyl, $C_{2-30}$-alkynyl and halogen, wherein $C_{6-26}$-arylene, optionally substituted with one to four substituents $R^d$, is selected from the group consisting of

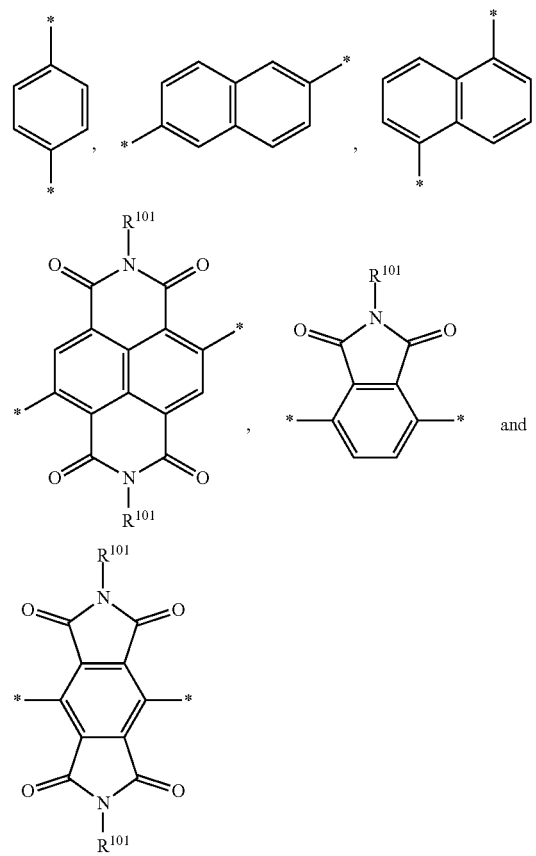

wherein $R^{101}$ is at each occurrence H or $C_{1-30}$-alkyl, and wherein 5 to 20 membered heteroarylene, optionally substituted with one to four substitutents $R^d$, are selected from the group consisting of

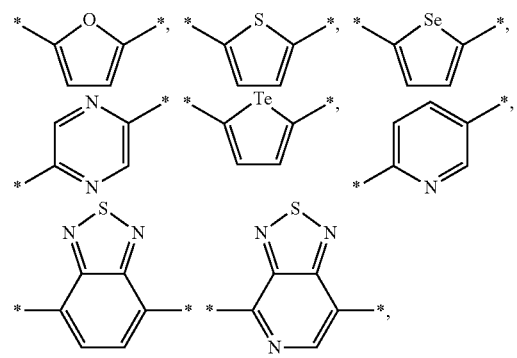

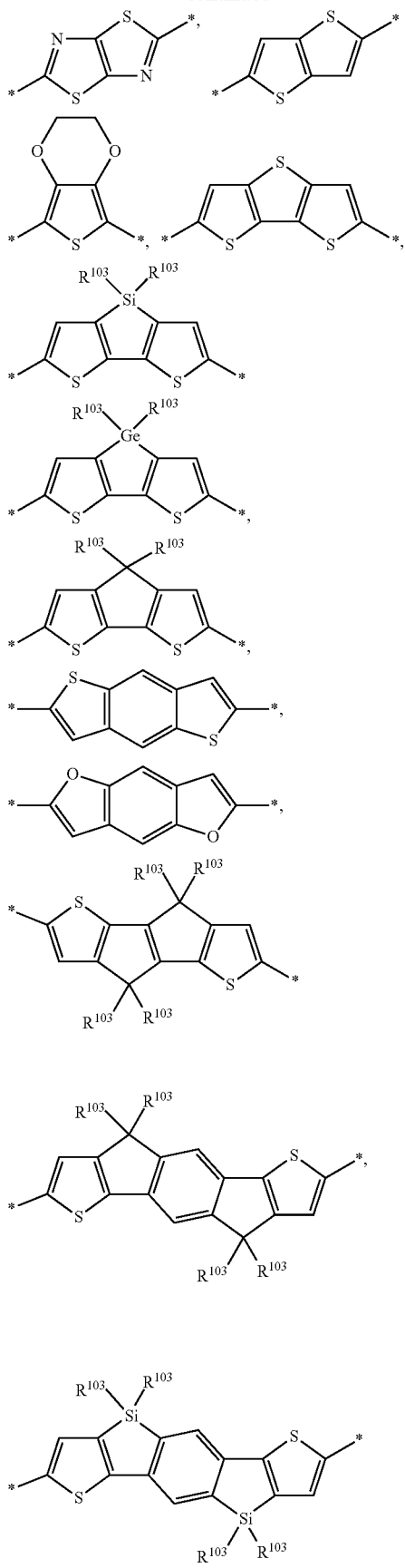

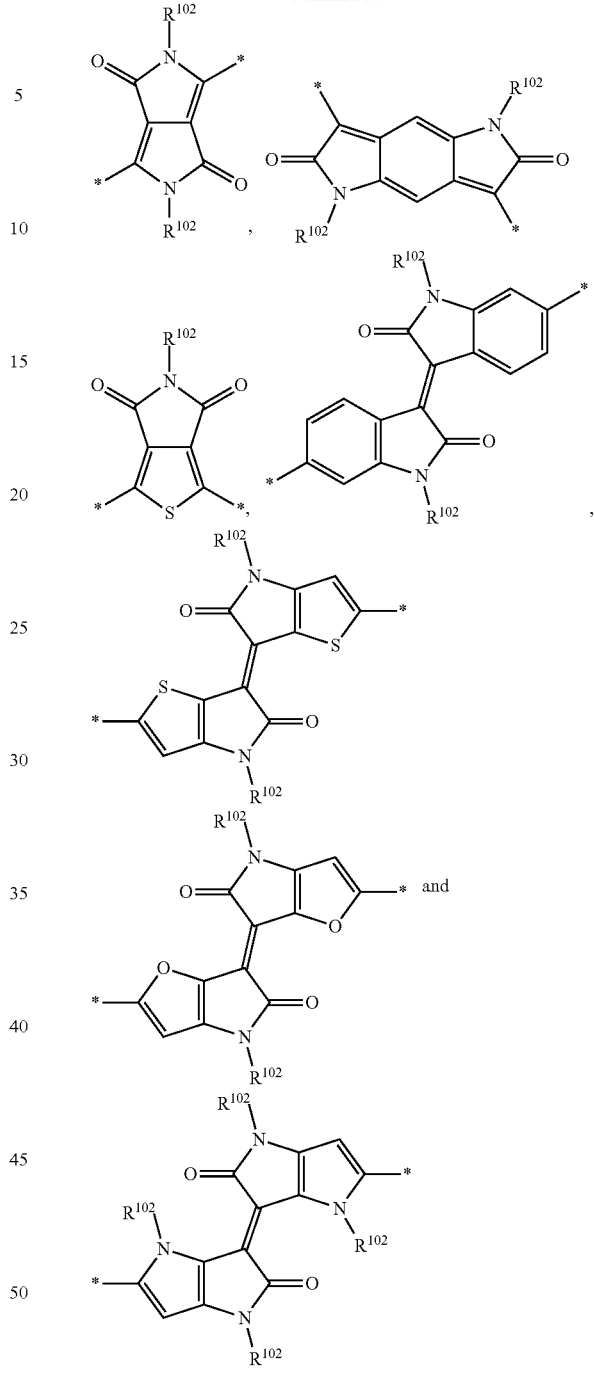

wherein
$R^{103}$ is at each occurrence H, $C_{1-30}$-alkyl, $C_{2-30}$-alkenyl or $C_{2-30}$-alkynyl or halogen,
$R^{102}$ is at each occurrence H or $C_{1-30}$-alkyl.

More preferably, $L^1$ and $L^2$ are independently from each other and at each occurrence selected from the group consisting of $C_{6-26}$-arylene, 5 to 20 membered heteroarylene wherein
$C_{6-26}$-arylene and 5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen, wherein $C_{6-26}$-arylene, optionally substituted with one to two substituents $R^d$, are selected from the group consisting of
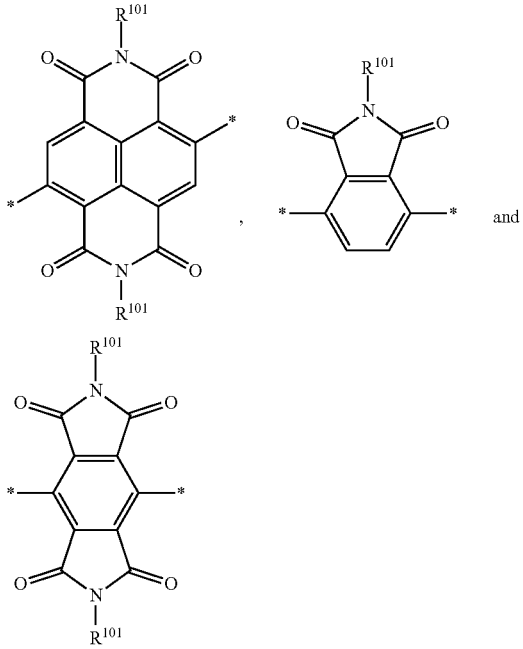
wherein
$R^{101}$ is at each occurrence H or $C_{1-30}$-alkyl,
and
wherein 5 to 20 membered heteroarylene, optionally substituted with one to two substituents $R^d$, are selected from the group consisting of
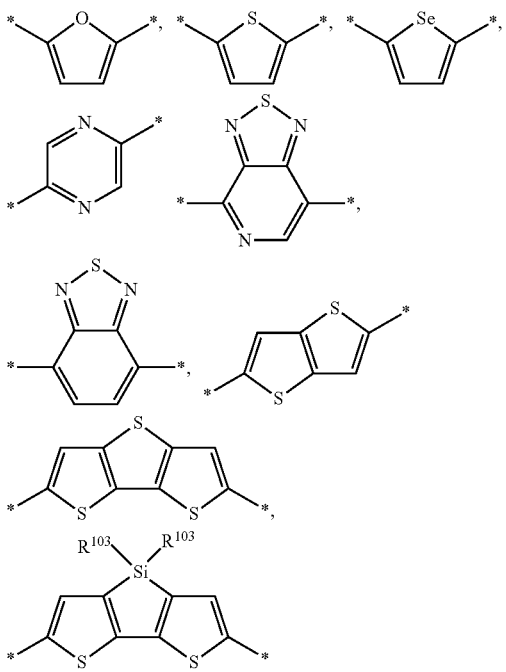
-continued
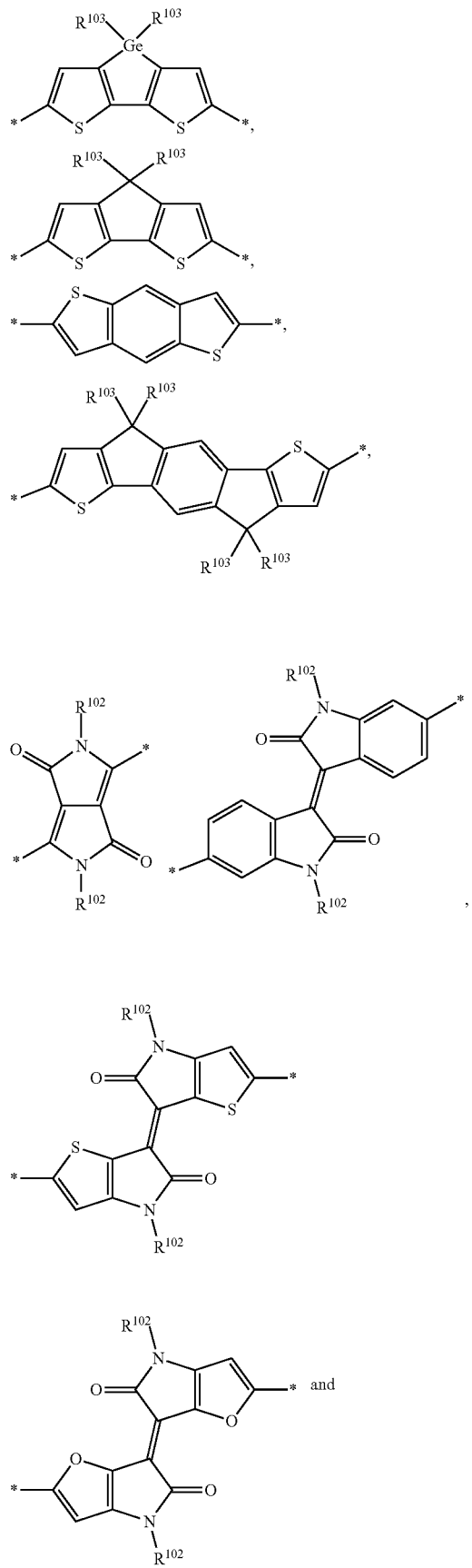

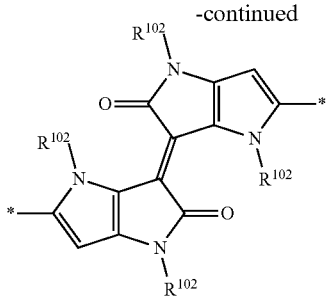

wherein
$R^{103}$ is at each occurrence H, $C_{1-30}$-alkyl, $C_{2-30}$-alkenyl or $C_{2-30}$-alkynyl or halogen,
$R^{102}$ is at each occurrence H or $C_{1-30}$-alkyl.

Even more preferably, $L^1$ and $L^2$ are independently from each other and at each occurrence selected from the group consisting of $C_{6-26}$-arylene, 5 to 20 membered heteroarylene wherein
$C_{6-26}$-arylene and 5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen,
wherein $C_{6-26}$-arylene, optionally substituted with one to two substituents $R^d$, is

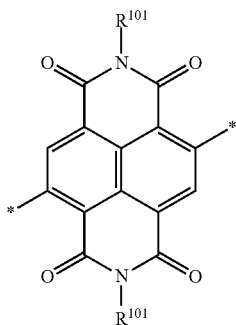

wherein
$R^{101}$ is at each occurrence H or $C_{1-30}$-alkyl,
and
wherein 5 to 20 membered heteroarylene, optionally substituted with one to two substitutents $R^d$, are selected from the group consisting of

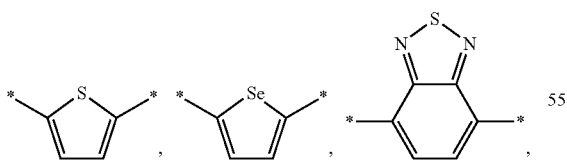

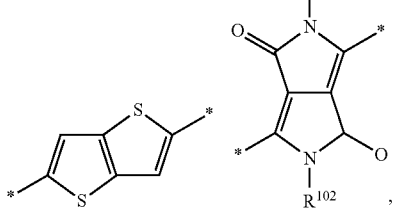

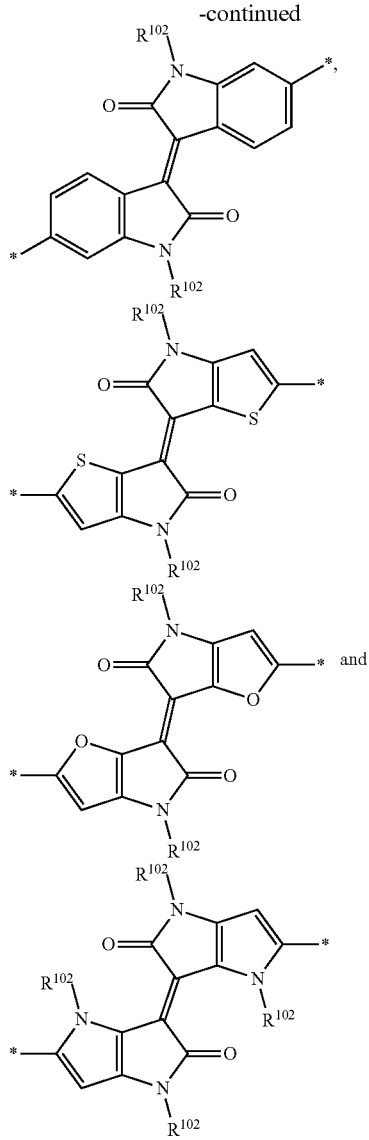

wherein
$R^{103}$ is at each occurrence H, $C_{1-30}$-alkyl, $C_{2-30}$-alkenyl or $C_{2-30}$-alkynyl or halogen,
$R^{102}$ is at each occurrence H or $C_{1-30}$-alkyl.

Most preferably, $L^1$ and $L^2$ are independently from each other a 5 to 20 membered heteroarylene
wherein
5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen,
wherein 5 to 20 membered heteroarylene, optionally substituted with one to two substitutents $R^d$, is

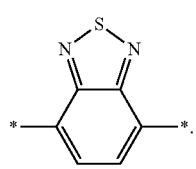

Particular preferred compounds of the present invention are polymers comprising at least one unit of formula 1 or 1', wherein n=0, and which are of formula
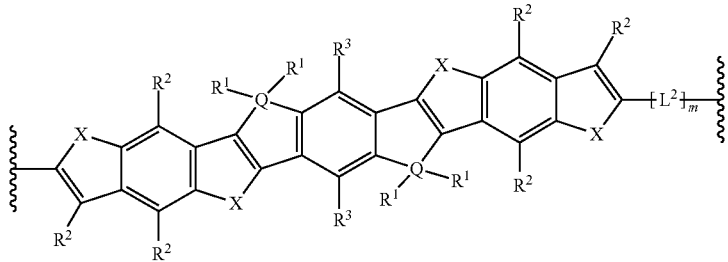
1-IA
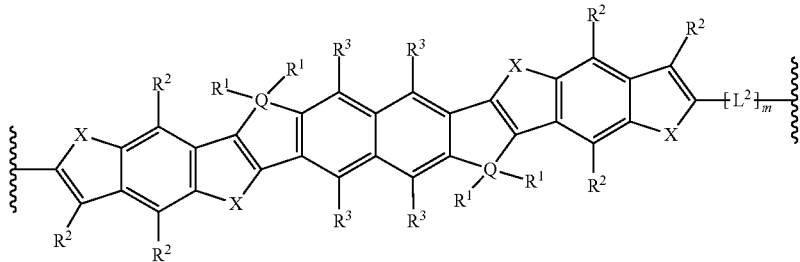
1-IB
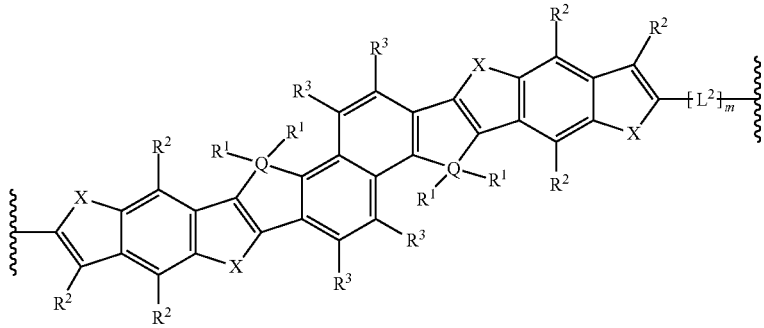
1-IC
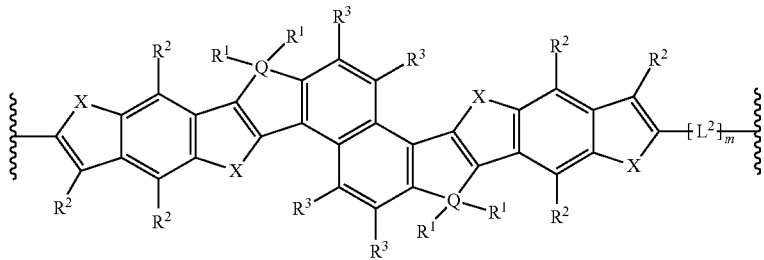
1-ID
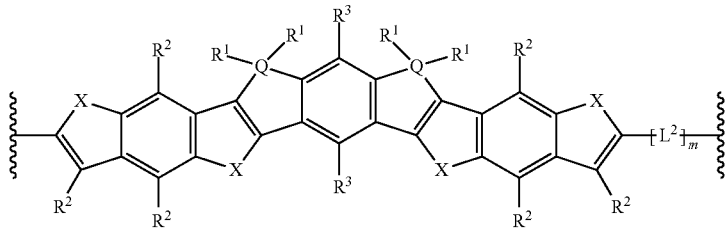
1'-IA -continued

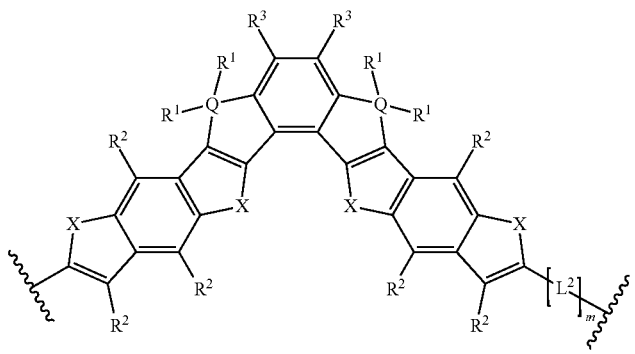

1'-IB

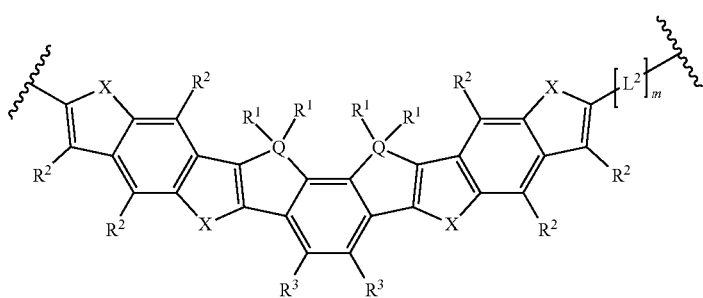

1'-IC wherein
X is at each occurrence O, S or Se,
Q is at each occurrence C or Si,
$R^1$ is at each occurrence $C_{1-50}$-alkyl,
$R^2$ is at each occurrence H,
m is 0, 1 or 2,
$L^2$ is at each occurrence selected from the group consisting of $C_{6-26}$-arylene, 5 to 20 membered heteroarylene wherein
  $C_{6-26}$-arylene and 5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen,
wherein $C_{6-26}$-arylene, optionally substituted with one to two substituents $R^d$, is

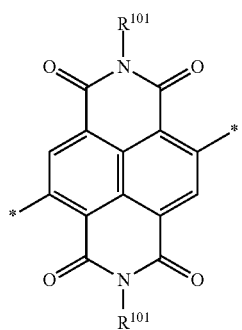

wherein
$R^{101}$ is at each occurrence H or $C_{1-30}$-alkyl,
and
wherein 5 to 20 membered heteroarylene, optionally substituted with one to two substituents $R^d$, are selected from the group consisting of

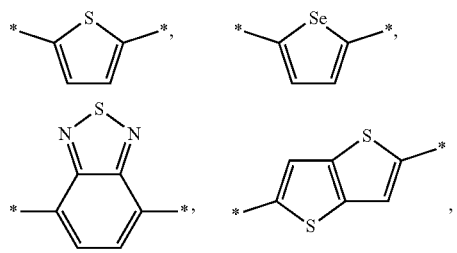

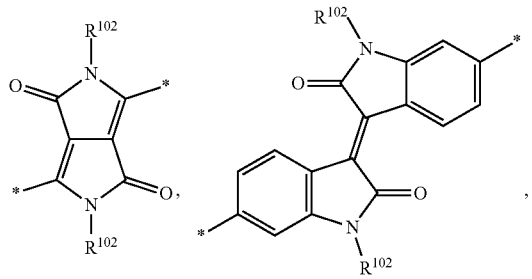

33
-continued
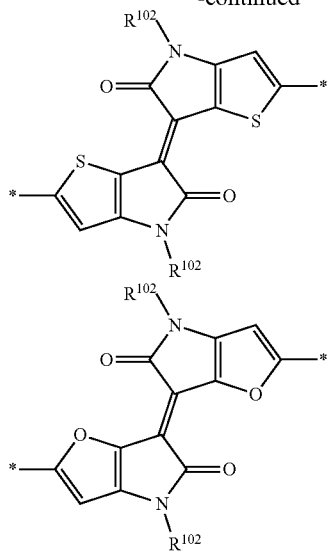
and
34
-continued
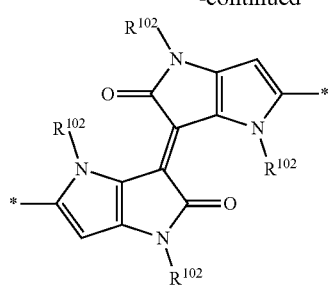
wherein
$R^{103}$ is at each occurrence H, $C_{1-30}$-alkyl, $C_{2-30}$-alkenyl or $C_{2-30}$-alkynyl or halogen,
$R^{102}$ is at each occurrence H or $C_{1-30}$-alkyl.
More particular preferred compounds of the present invention are polymers comprising at least one unit of formula 1 or 1', wherein n=0 and which are of formula
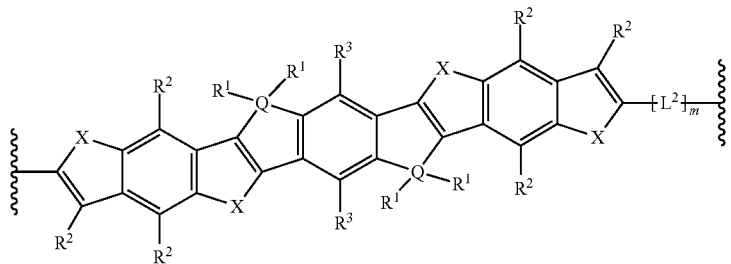
1-1A
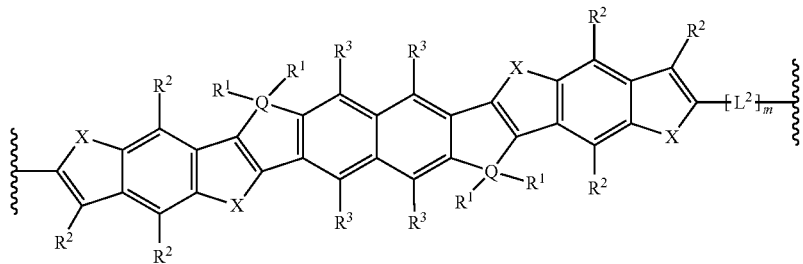
1-1B
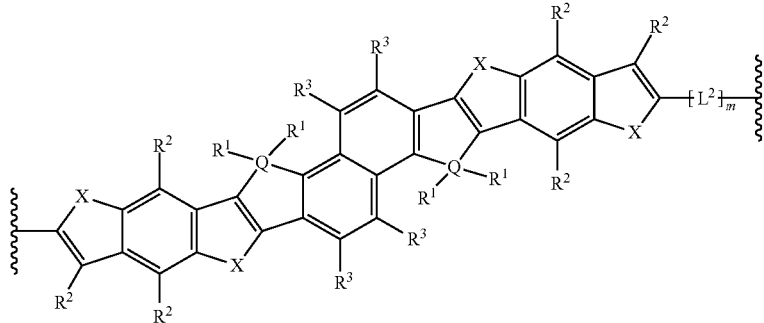
1-1C -continued 1-1D

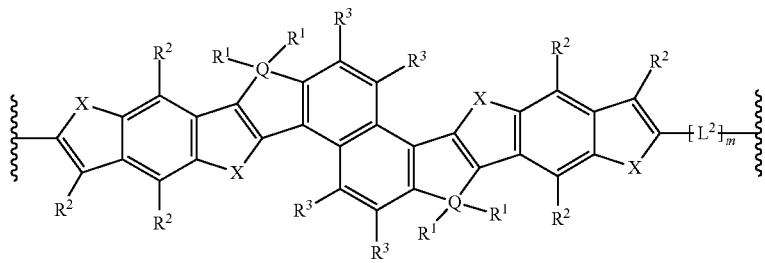

wherein

X is at each occurrence O, S or Se,

Q is at each occurrence C or Si, $R^1$ is at each occurrence $C_{1-50}$-alkyl, $R^2$ is at each occurrence H, m is 0, 1 or 2, $L^2$ is at each occurrence selected from the group consisting of $C_{6-26}$-arylene, 5 to 20 membered heteroarylene wherein $C_{6-26}$-arylene and 5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen, wherein $C_{6-26}$-arylene, optionally substituted with one to two substituents $R^d$, is

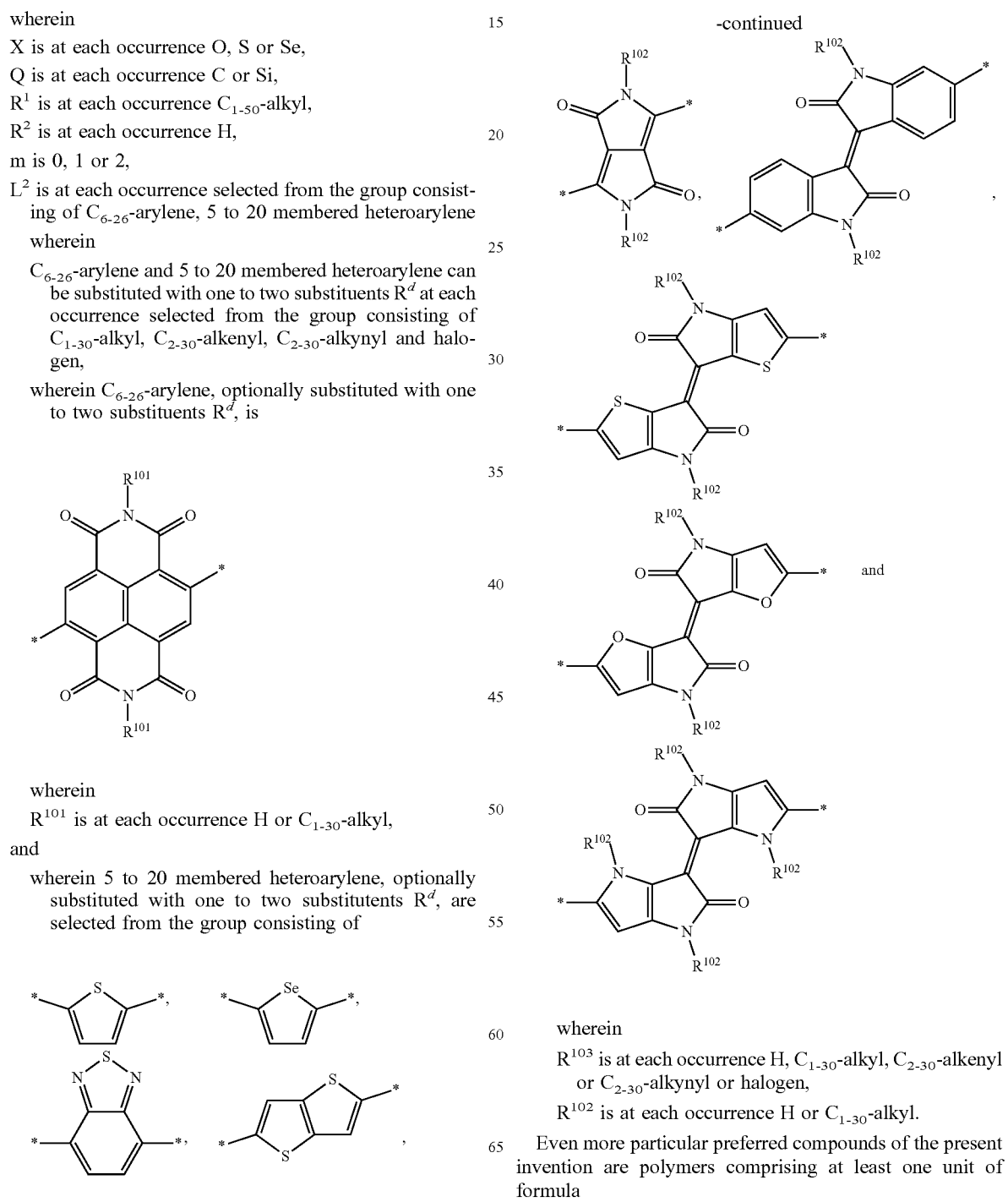

wherein $R^{101}$ is at each occurrence H or $C_{1-30}$-alkyl, and wherein 5 to 20 membered heteroarylene, optionally substituted with one to two substitutents $R^d$, are selected from the group consisting of wherein $R^{103}$ is at each occurrence H, $C_{1-30}$-alkyl, $C_{2-30}$-alkenyl or $C_{2-30}$-alkynyl or halogen, $R^{102}$ is at each occurrence H or $C_{1-30}$-alkyl.

Even more particular preferred compounds of the present invention are polymers comprising at least one unit of formula

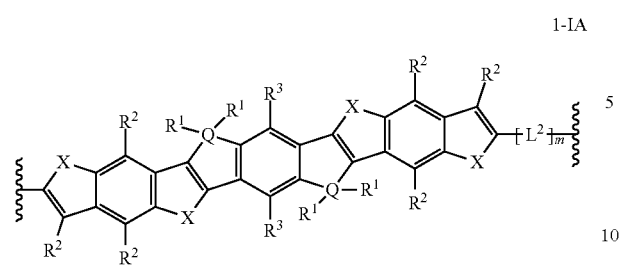

1-IA wherein

X is at each occurrence O, S or Se,

Q is at each occurrence C or Si, $R^1$ is at each occurrence $C_{1-50}$-alkyl, $R^2$ is at each occurrence H, m is 0, 1 or 2, $L^2$ is at each occurrence selected from the group consisting of $C_{6-26}$-arylene, 5 to 20 membered heteroarylene wherein $C_{6-26}$-arylene and 5 to 20 membered heteroarylene can be substituted with one to two substituents $R^d$ at each occurrence selected from the group consisting of $C_{1-30}$-alkyl, $C_{2-30}$-alkenyl, $C_{2-30}$-alkynyl and halogen, wherein $C_{6-26}$-arylene, optionally substituted with one to two substituents $R^d$, is

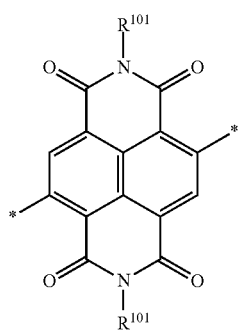

wherein $R^{101}$ is at each occurrence H or $C_{1-30}$-alkyl, and wherein 5 to 20 membered heteroarylene, optionally substituted with one to two substitutents $R^d$, are selected from the group consisting of

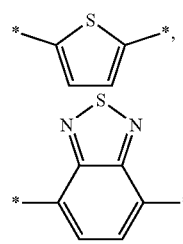

-continued

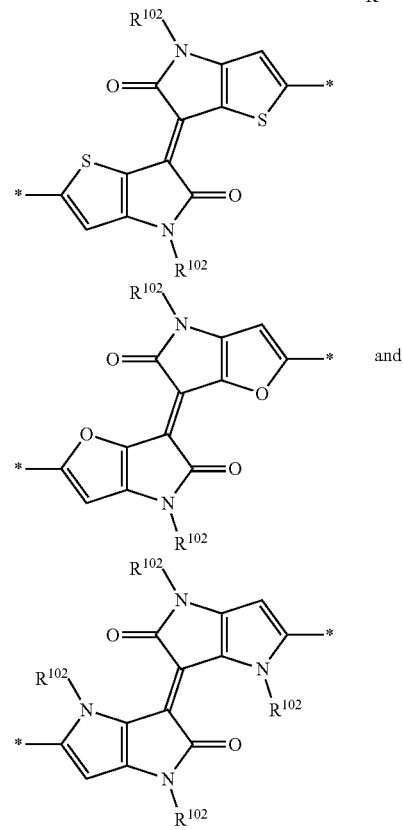

and wherein $R^{103}$ is at each occurrence H, $C_{1-30}$-alkyl, $C_{2-30}$-alkenyl or $C_{2-30}$-alkynyl or halogen, $R^{102}$ is at each occurrence H or $C_{1-30}$-alkyl.

Most particularly preferred compounds of the present invention are polymers comprising at least one unit of formula

1-IA

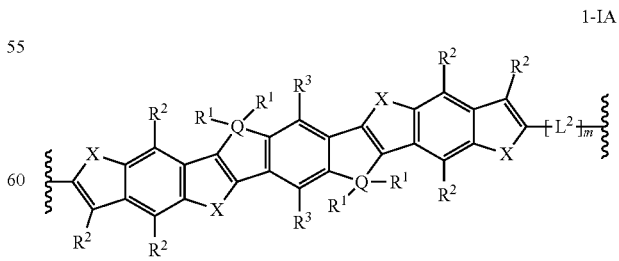

wherein

X is at each occurrence O, S or Se,

Q is at each occurrence C or Si, $R^1$ is at each occurrence $C_{1-50}$-alkyl,
$R^2$ is at each occurrence H,
m is 0, 1 or 2,
$L^2$ is at each occurrence 5 to 20 membered heteroarylene
wherein
5 to 20 membered heteroarylene can be substituted with one to two substituents $R^d$ which is at each occurrence halogen,
wherein 5 to 20 membered heteroarylene, optionally substituted with one to two substitutents $R^d$, is

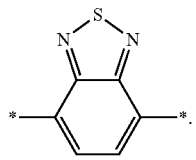

Especially preferred compounds of the present invention are polymers comprising at least one unit of formula

1-IA1

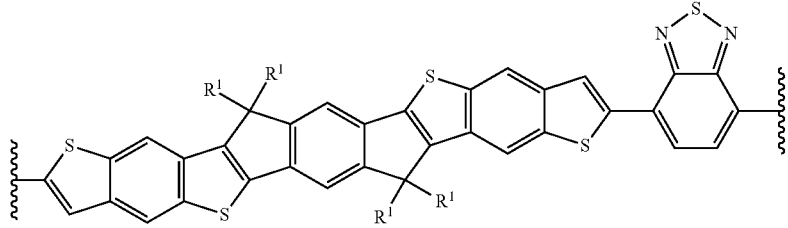

wherein $R^1$ is at each occurrence $C_{1-50}$-alkyl.

Also part of the present invention, is a process for the preparation of the compounds of the present invention comprising at least one unit of formula

1

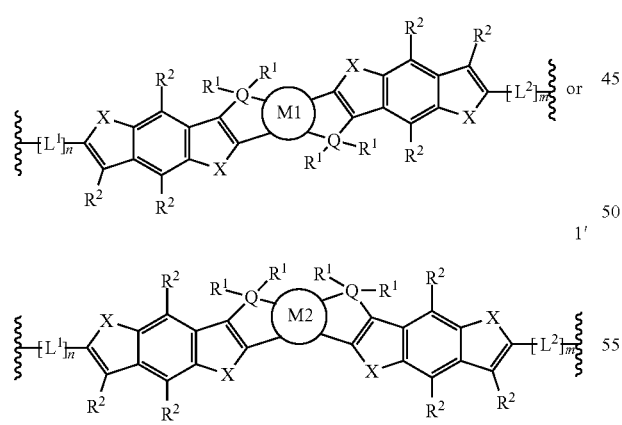

1' wherein
M1 and M2 are independently of each other an aromatic or heteroaromatic monocyclic or bicyclic ring system;
X is at each occurrence O, S, Se or Te,
Q is at each occurrence C, Si or Ge,
$R^1$ is at each occurrence selected from the group consisting of H, $C_{1-50}$-alkyl, —[CH$_2$]$_o$—[OSiR$^a$R$^a$]$_o$—OSiR$^a$-R$^a$R$^a$, —[CH$_2$]$_o$—[R$^a$R$^a$Si—O]$_p$—SiR$^a$R$^a$R$^a$, —[CR$^b$R$^b$]$_q$—CR$^b$R$^b$R$^b$, $C_{2-50}$-alkenyl, $C_{2-50}$-alkynyl, $C_{5-8}$-cycloalkyl, $C_{6-14}$-aryl and 5 to 14 membered heteroaryl,
wherein
is an integer from 0 to 10,
p is an integer from 1 to 40,
$R^a$ is at each occurrence $C_{1-10}$-alkyl, $C_{2-10}$-alkenyl or $C_{2-10}$-alkynyl,
q is an integer from 1 to 50,
$R^b$ is at each occurrence H or halogen, with the provisio that not all $R^b$ in —[CR$^b$R$^b$]$_q$—CR$^b$R$^b$R$^b$ are H,
$C_{1-50}$-alkyl, $C_{2-50}$-alkenyl and $C_{2-50}$-alkynyl can be substituted with one to four substituents independently selected from the group consisting of OR$^c$, OC(O)—R$^c$, C(O)—OR$^c$, C(O)—R$^c$, NR$^c$R$^c$, NR$^c$—C(O)R$^c$, C(O)—NR$^c$R$^c$, N[C(O)R$^c$][C(O)R$^c$], SR$^c$, CN, SiR$^c$R$^c$R$^c$, and NO$_2$,
$C_{5-8}$-cycloalkyl can be substituted with one or two substituents independently selected from the group consisting of $C_{1-10}$-alkyl, $C_{2-10}$-alkenyl, $C_{2-10}$-alkynyl, OR$^c$, OC(O)—R$^c$, C(O)—OR$^c$, C(O)—R$^c$, NR$^c$R$^c$, NR$^c$—C(O)R$^c$, C(O)—NR$^c$R$^c$, N[C(O)R$^c$][C(O)R$^c$], SR$^c$, halogen, CN, SiR$^c$R$^c$R$^c$, and NO$_2$; and one CH$_2$-group of $C_{5-8}$-cycloalkyl can be replaced by O, S, OC(O), CO, NR$^c$ or NR$^c$—CO,
$C_{6-14}$-aryl and 5 to 14 membered heteroaryl can be substituted with one to three substituents independently selected from the group consisting of $C_{1-10}$-alkyl, $C_{2-10}$-alkenyl, $C_{2-10}$-alkynyl, OR$^c$, OC(O)—R$^c$, C(O)—OR$^c$, C(O)—R$^c$, NR$^c$R$^c$, NR$^c$—C(O)R$^c$, C(O)—NR$^c$R$^c$, N[C(O)R$^c$][C(O)R$^c$], SR$^c$, halogen, CN, and NO$_2$,
wherein
$R^c$ is at each occurrence H, $C_{1-20}$-alkyl, $C_{2-10}$-alkenyl or $C_{2-10}$-alkynyl,
$R^2$ is at each occurrence H, $C_{1-30}$-alkyl, $C_{2-30}$-alkenyl or $C_{2-30}$-alkynyl or halogen,
n is 0, 1, 2, 3 or 4,
m is 0, 1, 2, 3 or 4,
and
$L^1$ and $L^2$ are independently from each other and at each occurrence selected from the group consisting of $C_{6-26}$-arylene, 5 to 20 membered heteroarylene,

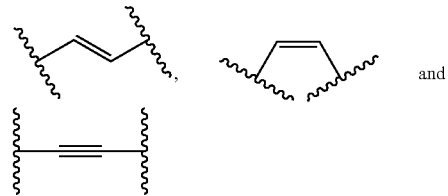

wherein

C$_{6-26}$-arylene and 5 to 20 membered heteroarylene can be substituted with one to four substituents R$^d$ at each occurrence selected from the group consisting of H, C$_{1-30}$-alkyl, C$_{2-30}$-alkenyl, C$_{2-30}$-alkynyl and halogen, and

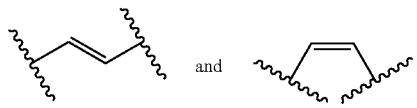

can be substituted with one or two substituents at each occurrence selected from the group consisting of R$^e$, COOR$^e$ and CN, wherein R$^e$ is at each occurrence selected from the group consisting of H, C$_{1-30}$-alkyl, C$_{2-30}$-alkenyl and C$_{2-30}$-alkynyl, which process comprises the step of treating a compound of formula

4

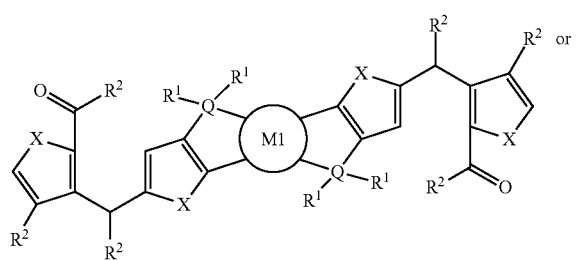

4'

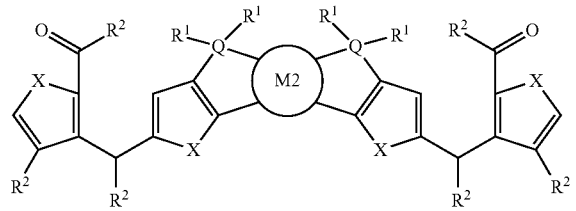

wherein M1, M2, X, Q, R$^1$ and R$^2$ are as defined for units of formula 1 or 1' with acid to afford a compound of formula

3

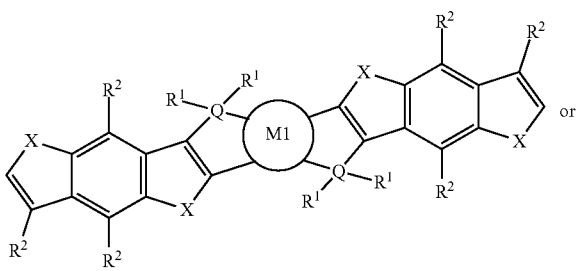

or

3'

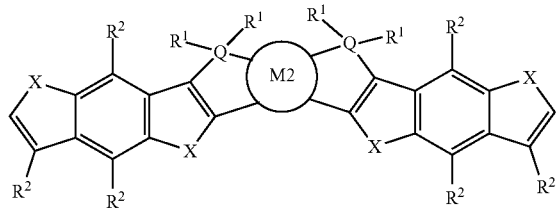

wherein M1, M2, X, Q, R$^1$ and R$^2$ are as defined for the units of formula 1 and 1'.

The acid can be any acid such as a cation exchanger in hydrogen form, trifluoroacetic acid, acetic acid or p-toluene sulfonic acid. Preferably, the acid is a cation exchanger in hydrogen form, more preferably Amberlyst® 15.

Preferably, the water formed in this step is removed in situ.

The step can be performed in any suitable solvent, for example toluene.

The compounds of the present invention comprising at least one unit of formula 1 or 1' can be prepared from compounds of formula 3 or 3' by methods known in the art.

The compounds of the present invention, which are polymers comprising at least a unit of formula 1 or 1', wherein n=0, and which are units of formula

1-I

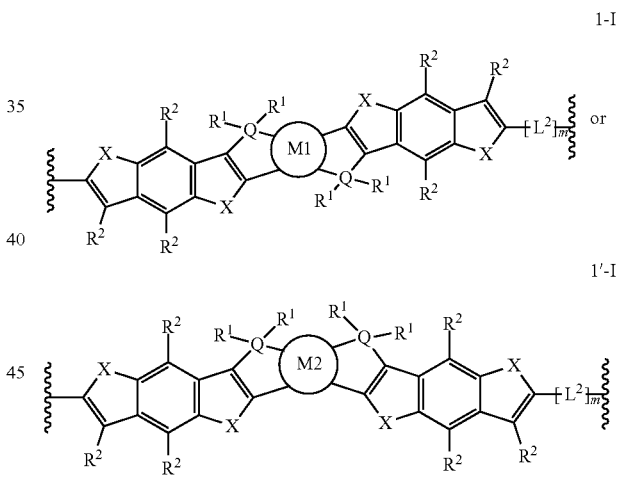

or

1'-I

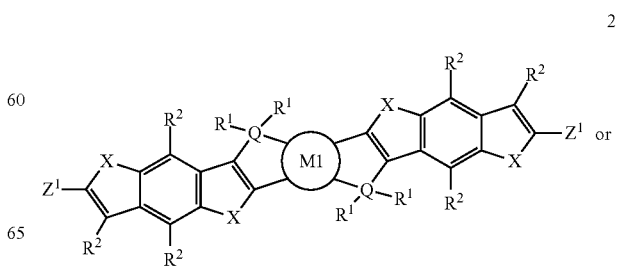

wherein

M1, M2, X, Q, R$^1$, R$^2$, m and L$^2$ are as defined for a formula 1 or 1', can be prepared by treating a compound of formula

2

-continued

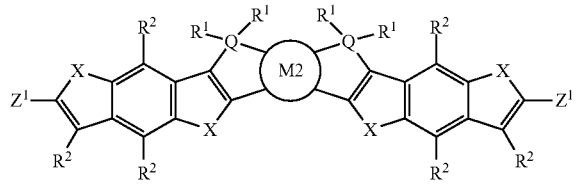

wherein M1, M2, X, Q, $R^1$ and $R^2$ are as defined for units of formula 1 or 1', and
$Z^1$ is at each occurrence selected from h group consisting of $B(OZ^a)(OZ^a)$, $SnZ^aZ^aZ^a$,

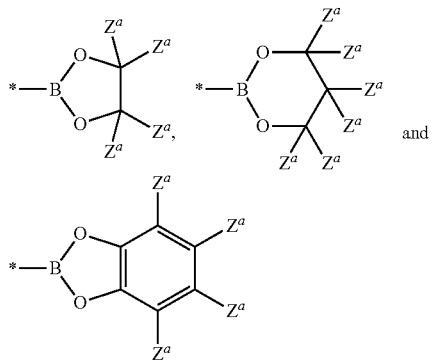

wherein $Z^a$ is at each occurrence H or $C_{1-4}$-alkyl, with a compound of formula $LG^2-L^2-LG^2$ wherein $L^2$ is as defined in units of formula 1 and 1', and $LG^2$ is at each occurrence a leaving group.

For example, the compounds of the present invention, which are polymers comprising at least a unit of formula 1 or 1', wherein n and m=0 and which units are of formula

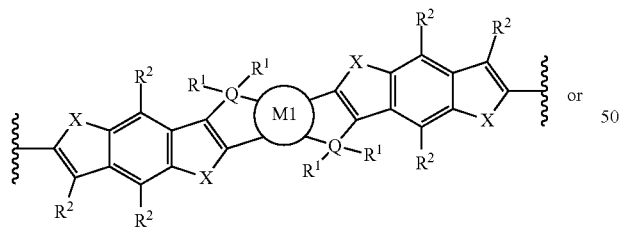

1-II or

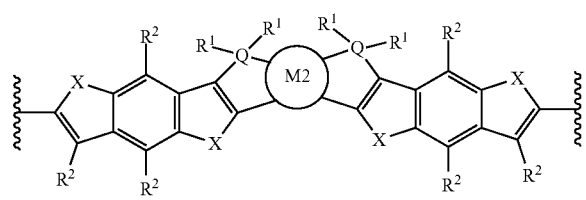

1'-II wherein
M1, M2, X, Q, $R^1$ and $R^2$ are defined as in formula 1 or 1, can be prepared by treating a compound of formula

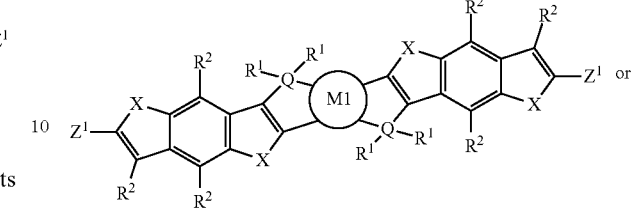

2 or

2'

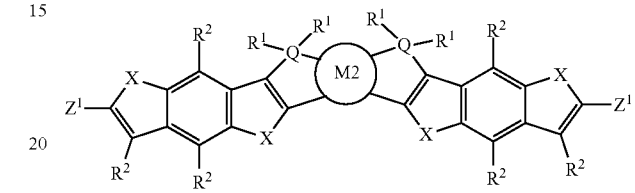

wherein M1, M2, X, Q, $R^1$ and $R^2$ are defined as in formula 1 or 1', and
$Z^1$ is at each occurrence selected from the group consisting of $B(OZ^a)(OZ^a)$, $SnZ^aZ^aZ^a$,

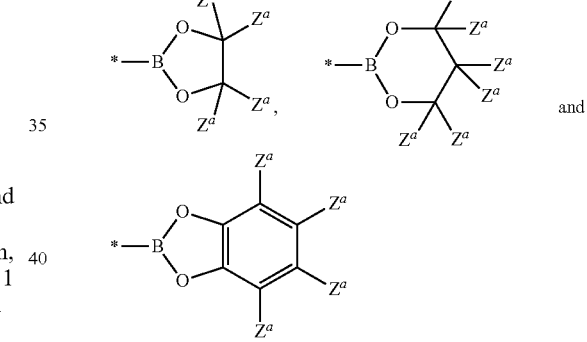

wherein $Z^a$ is at each occurrence H or $C_{1-4}$-alkyl, with a compound of formula

16 or

16' wherein M1, M2, X, Q, $R^1$ and $R^2$ are defined as in formula 1 or 1', and $LG^3$ is a leaving group.

Preferably, $Z^1$ is at each occurrence selected from the group consisting of $SnZ^aZ^aZ^a$ and

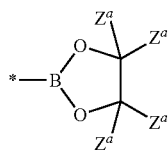

wherein $Z^a$ is at each occurrence H or $C_{1-4}$-alkyl.

More preferably, $Z^1$ is at each occurrence $SnZ^aZ^aZ^a$, wherein $Z^a$ is at each occurrence $C_{1-4}$-alkyl.

Preferably, $LG^2$ and $LG^3$ are independently and at each occurrence halogen, more preferably Cl or Br.

The reaction is usually performed in the presence of a catalyst, preferably a Pd catalyst such as $Pd(P(Ph)_3)_4$, $Pd(OAc)_2$ and tris(dibenzylideneacetone)dipalladium. Depending on the Pd catalyst, the reaction may also require the presence of a phosphine ligand such as $P(Ph)_3$, $P(o\text{-}tolyl)_3$ and $P(tert\text{-}Bu)_3$. The reaction is also usually performed at elevated temperatures, such as at temperatures in the range of 40 to 250° C., preferably 60 to 200° C. The reaction can be performed in the presence of any suitable solvent such as tetrahydrofuran, toluene or chlorobenzene. The reaction is usually performed under inert gas.

When $Z^1$ is at each occurrence $SnZ^aZ^aZ^a$, wherein $Z^a$ is at each occurrence $C_{1-4}$-alkyl, the reaction is usually performed in the presence of a catalyst, preferably a Pd catalyst such as $Pd(P(Ph)_3)_4$ and tris(dibenzylideneacetone)dipalladium.

The compounds of formula

2

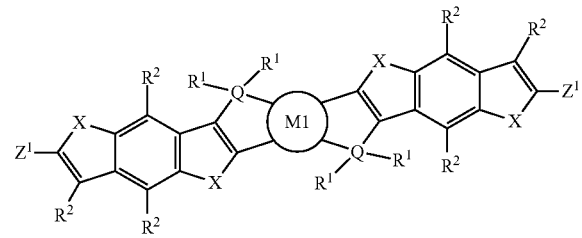

2'

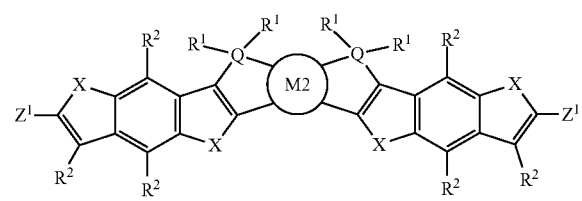

wherein M1, M2, X, Q, $R^1$ and $R^2$ are as defined for units of formula 1 and 1', and $Z^1$ is at each occurrence selected from the group consisting of $B(OZ^a)(OZ^a)$, $SnZ^aZ^aZ^a$,

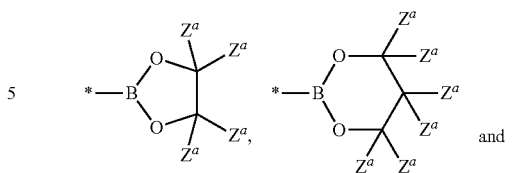

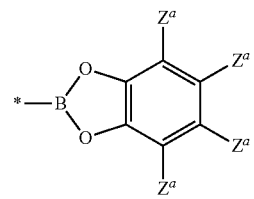

wherein $Z^a$ is at each occurrence H or $C_{1-4}$-alkyl, can be prepared by treating a compound of formula

3

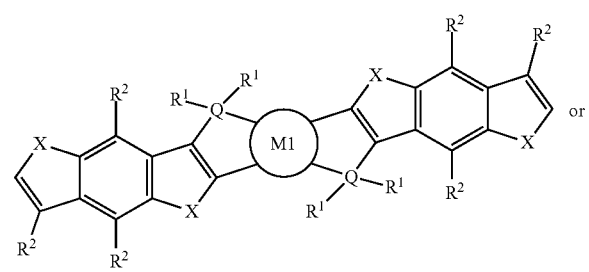

or

3'

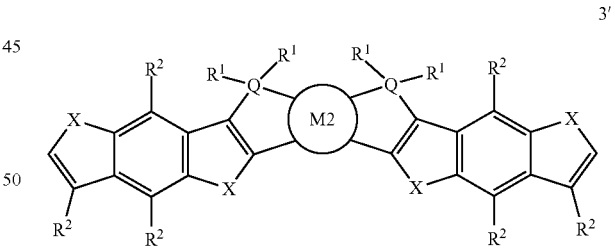

wherein M1, M2, X, Q, $R^1$ and $R^2$ are as defined for units of formula 1 or 1', with a base and $Z^1\text{-}LG^1$, wherein $Z^1$ is as defined in formula 2 or 2', and $LG^1$ is a leaving group.

The base can be any suitable base such as n-butyl lithium.

Preferably, if $Z^1$ is $SnZ^aZ^aZ^a$, $LG^1$ is at each occurrence halogen, more preferably Br.

The compounds of formula 4, wherein M1, Q, X, $R^1$ and $R^2$ are as defined for the units of formula 1, can be prepared as follows

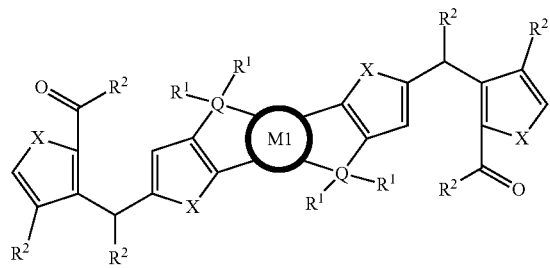
4
↑ Dess-Martin Periodinane
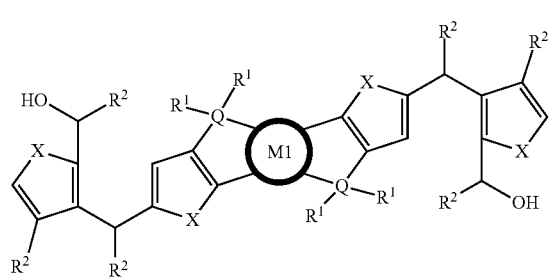
5
↑ TBAF
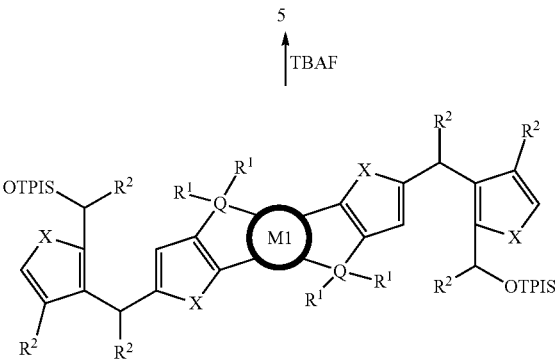
6
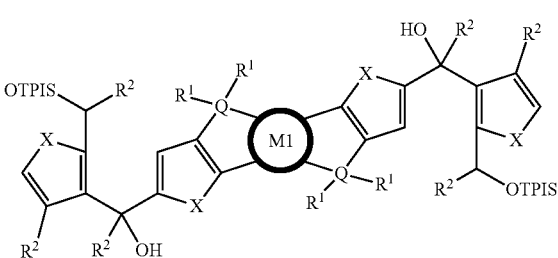
↑ ZnI$_2$, NaBH$_3$CN
7
↑
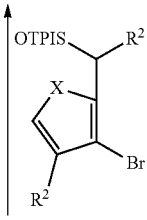
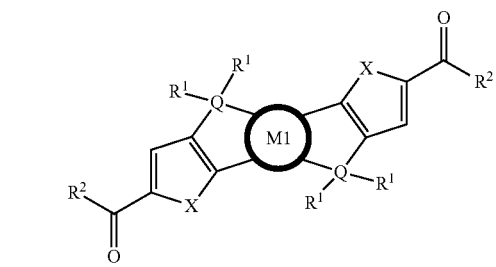
8
The compounds of formula 8, wherein M1, Q, X and R$^1$ are as defined for the units of formula 1 and R$^2$ is H, can be prepared as follows
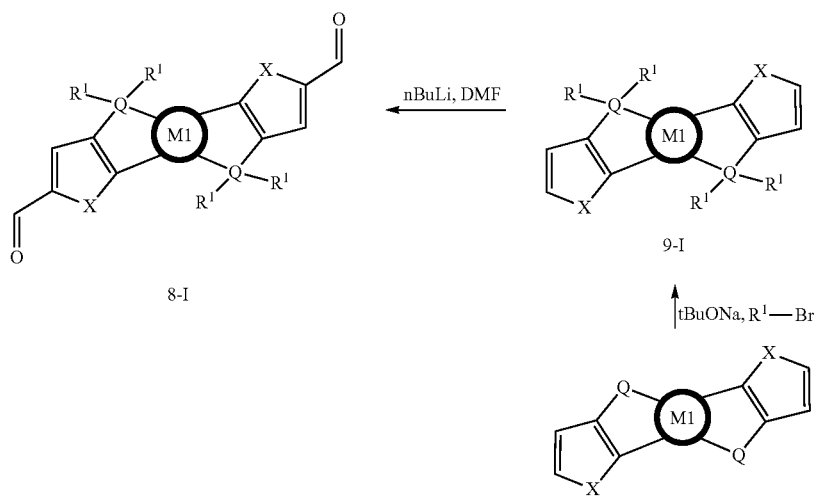
↑ tBuONa, R$^1$—Br
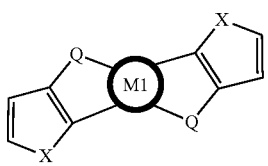
10-I The compounds of formula 4', wherein M2, Q, X, R¹ and R² are as defined for the units of formula 1' and can be prepared as follows:
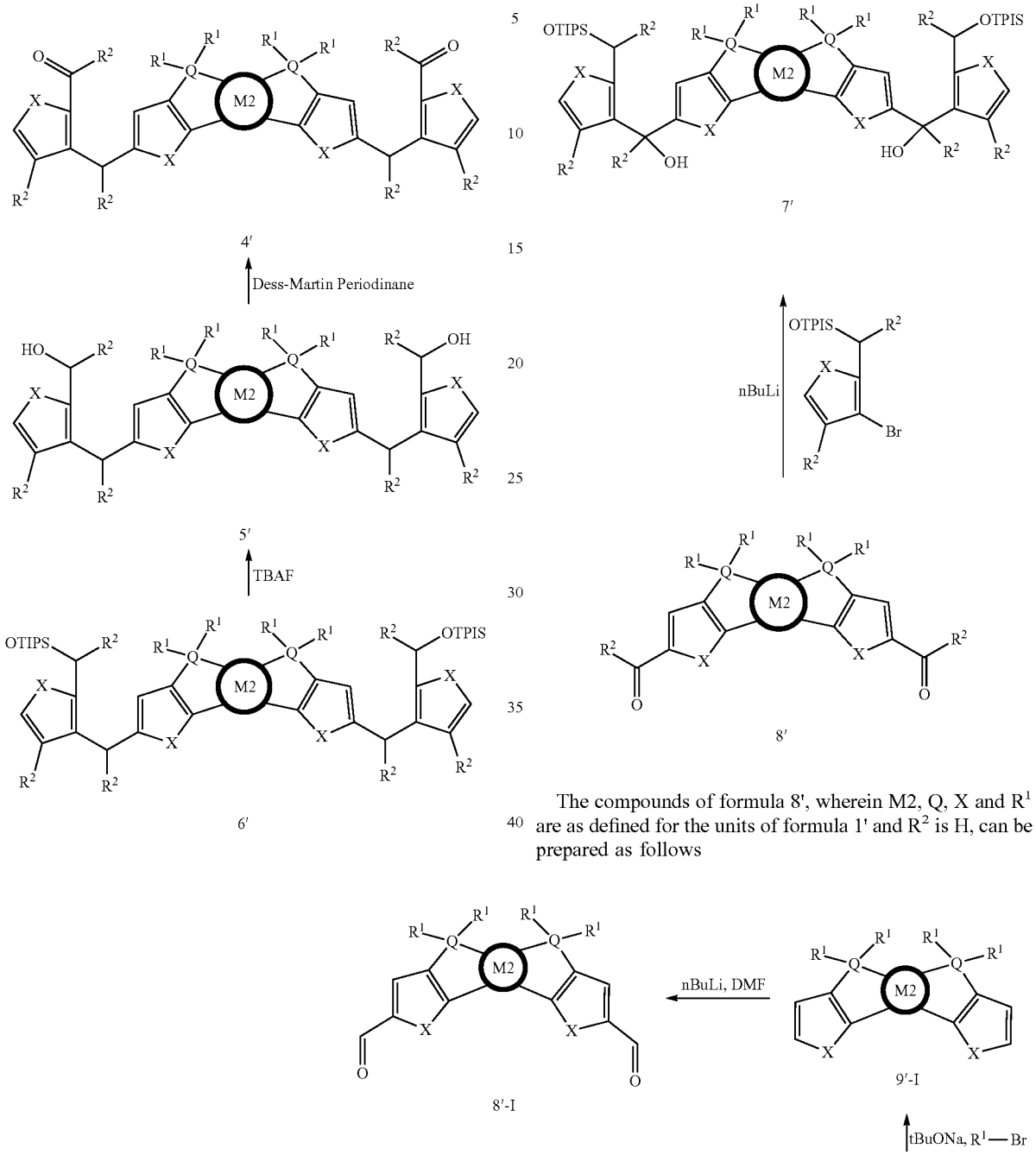
The compounds of formula 8', wherein M2, Q, X and R¹ are as defined for the units of formula 1' and R² is H, can be prepared as follows
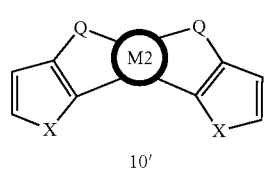

The compounds 10 and 10' can be prepared by methods known in the art, for example as described in W. Zhang, J. Smith, S. E. Watkins, R. Gysel, M. McGehee, A. Salleo, J. Kirkpatrick, S. Ashraf, T. Anthopoulos, M. Heeney, I. McCulloch, *J. Am. Chem. Soc.* 2010, 132, 11437.

Also part of the present invention are compounds of formula

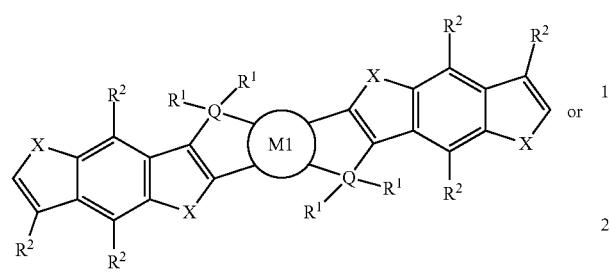

3 or

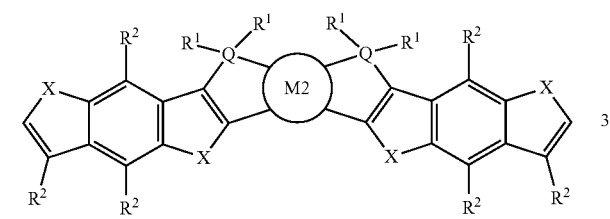

3' wherein M1, M2, X, Q, $R^1$ and $R^2$ are as defined for the units of formula 1 or 1'.

Preferred compounds of formula 3 or 3' are of formula

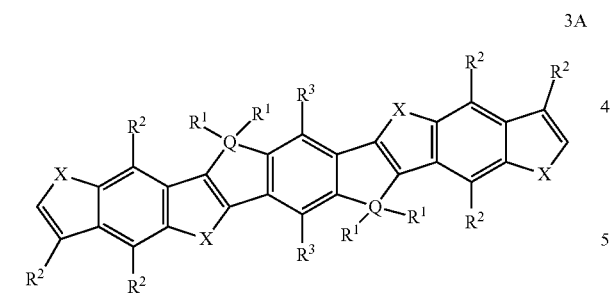

3A

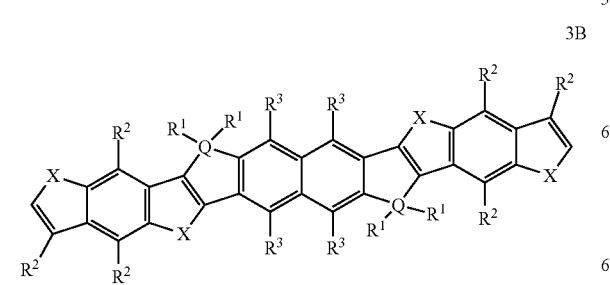

3B

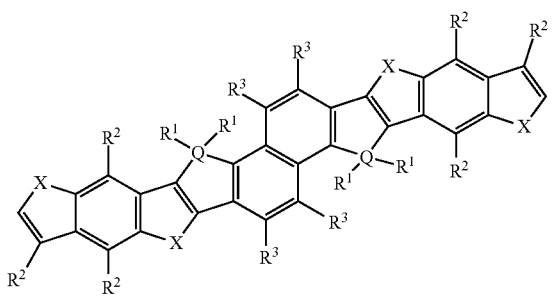

3C

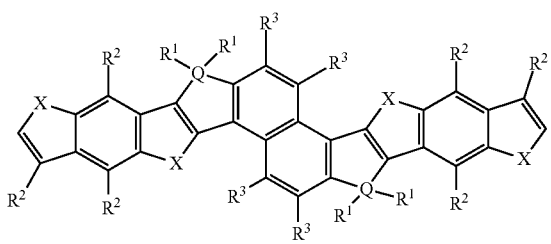

3D

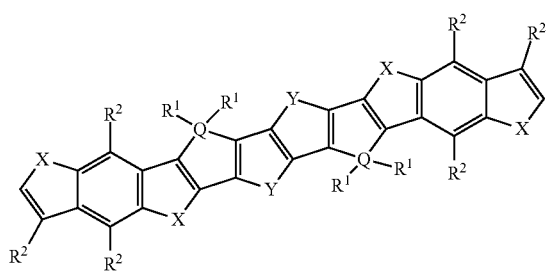

3E

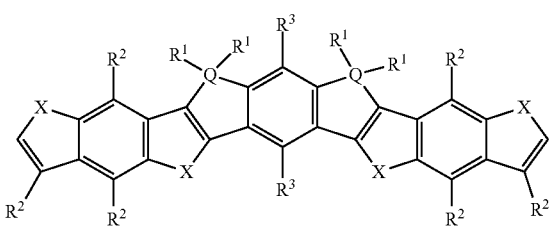

3'A

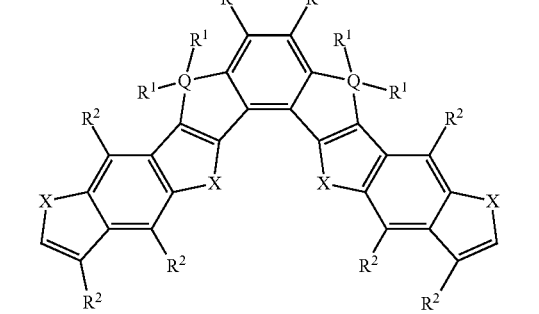

3'B

-continued

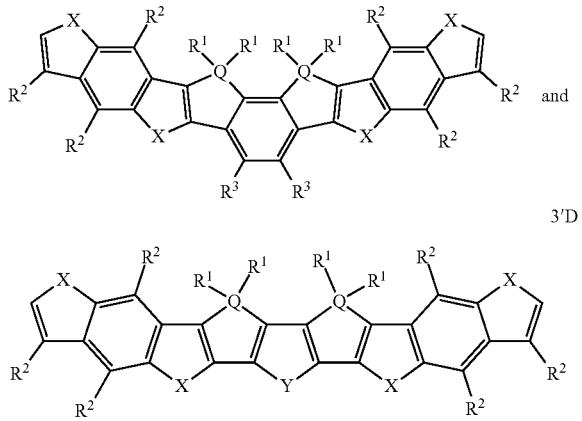

wherein
X, Q, R¹ and R² are as defined above, and
Y is at each occurrence O, S, Se or Te, and
R³ is at each occurrence H, $C_{1-30}$-alkyl, $C_{2-30}$-alkenyl or $C_{2-30}$-alkynyl or halogen.

More preferred compounds of formula 3 or 3' are compounds of formula 3A, 3B, 3C, 3D, 3'A, 3'B and 3'C.

Even more preferred compounds of formula 3 or 3' are compounds of formula 3A, 3B, 3C and 3D.

Most preferred compounds of formula 3 or 3' are compounds of formula 3A.

Also part of the invention is an electronic device comprising the compounds of the present invention.

The electronic device can be an organic photovoltaic device (OPVs), an organic field-effect transistor (OFETs), an organic light emitting diode (OLEDs) or an organic photodiode (OPDs).

Preferably, the electronic device is an organic photovoltaic device (OPVs), an organic field-effect transistor (OFETs) or an organic photodiode (OPDs).

More preferably, the electronic device is an organic field effect transistor (OFET).

Usually, an organic field effect transistor comprises a dielectric layer, a semiconducting layer and a substrate. In addition, an organic field effect transistor usually comprises a gate electrode and source/drain electrodes.

Preferably, the semiconducting layer comprises the compounds of the present invention. The semiconducting layer can have a thickness of 5 to 500 nm, preferably of 10 to 100 nm, more preferably of 20 to 50 nm.

The dielectric layer comprises a dielectric material. The dielectric material can be silicon dioxide or aluminium oxide, or, an organic polymer such as polystyrene (PS), poly(methylmethacrylate) (PMMA), poly(4-vinylphenol) (PVP), poly(vinyl alcohol) (PVA), benzocyclobutene (BCB), fluoropolymers or polyimide (PI). The dielectric layer can have a thickness of 10 to 2000 nm, preferably of 50 to 1000 nm, more preferably of 100 to 800 nm.

The dielectric layer can in addition to the dielectric material comprise a self-assembled monolayer of organic silane derivates or organic phosphoric acid derivatives. An example of an organic silane derivative is octyltrichlorosilane. An examples of an organic phosphoric acid derivative is octyldecylphosphoric acid. The self-assembled monolayer comprised in the dielectric layer is usually in contact with the semiconducting layer.

The source/drain electrodes can be made from any suitable organic or inorganic source/drain material. Examples of inorganic source/drain materials are gold (Au), silver (Ag) or copper (Cu), as well as alloys comprising at least one of these metals. The source/drain electrodes can have a thickness of 1 to 100 nm, preferably from 20 to 70 nm.

The gate electrode can be made from any suitable gate material such as highly doped silicon, aluminium (Al), tungsten (W), indium tin oxide or gold (Au), or alloys comprising at least one of these metals. The gate electrode can have a thickness of 1 to 200 nm, preferably from 5 to 100 nm.

The substrate can be any suitable substrate such as glass, or a plastic substrate such as polyethersulfone, polycarbonate, polysulfone, polyethylene terephthalate (PET) and polyethylene naphthalate (PEN). Depending on the design of the organic field effect transistor, the gate electrode, for example highly doped silicon can also function as substrate.

The organic field effect transistor can be prepared by methods known in the art.

For example, a top-gate bottom-contact organic field effect transistor can be prepared as follows: Source/drain electrodes can be formed by evaporating a suitable source/drain material, for example gold (Au), on photo-lithographically defined electrodes on a suitable substrate, for example a glass substrate. The electrodes can be treated with a suitable electrode treatment material such as pentafluorobenzenethiol. The semiconducting layer can be formed by depositing a solution of the compounds of the present invention, for example by spin-coating, on the source/drain electrodes. A dielectric layer can be formed by applying, for example, by spin-coating, a solution of a suitable dielectric material such as fluoropolymer, on the semiconducting layer. The gate electrode of a suitable gate material, for example gold (Au), can be evaporated through a shadow mask on the dielectric layer.

Also part of the invention is the use of the compounds of the present invention as semiconducting material.

The compounds of the present invention show high charge carrier mobilities. In addition, the compounds of the present invention show a high stability. Furthermore, the polymers of the present invention are compatible with liquid processing techniques.

Figure 2:
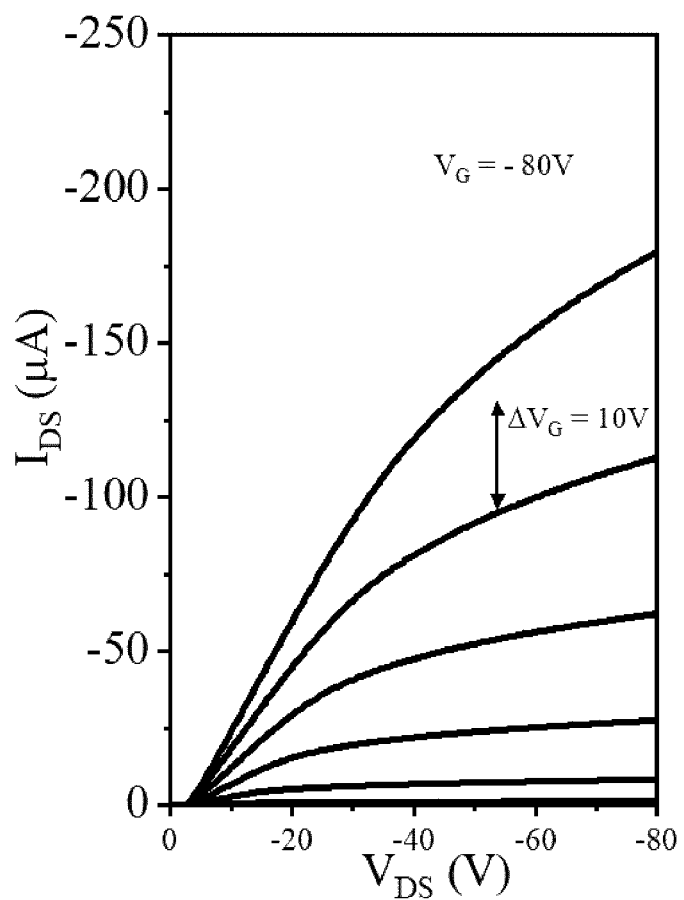

FIG. 1 shows the transfer characteristics of an organic field effect transistor comprising polymer P1 as semiconducting material FIG. 2 shows the output characteristics of an organic field effect transistor comprising polymer P1 as semiconducting material.

EXAMPLES

Example 1

Preparation of Compound 11a

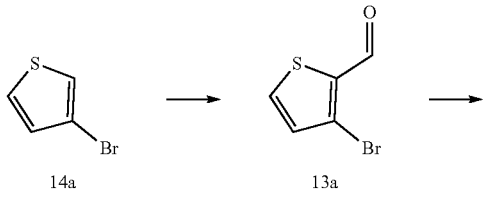

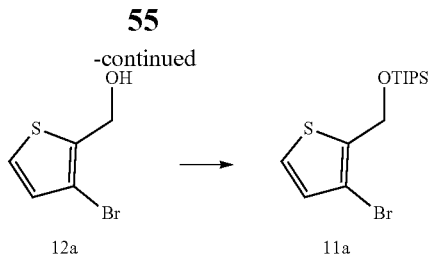

Compound 13a: A solution of LDA in THF (1 M) (67.4 mL, 67.4 mmol) was added dropwise to 3-bromothiophene (14a) (10 g, 61.3 mmol) in 300 mL THF at 0° C. After stirring the mixture for 1 h, DMF (5.2 mL, 67.4 mmol) was added to the mixture at 0° C. and the mixture was warmed up to room temperature. After stirring for 4 h, water (100 mL) was added to the mixture and it was extracted with ether for three times. The organic phases were collected, dried over magnesium sulfate, filtered and concentrated under vacuum. The product was purified by column chromatography on silica gel with hexane/ethyl acetate (50:1) as eluent to give compound 13a as a yellow oil. Yield: 11.0 g (94%). $^1$H NMR (400 MHz; CDCl$_3$): δ 7.15 (d, 1H, J=4.8 Hz), 7.73 (dd, 1H, J=1.2, 5.2 Hz), 9.98 (d, 1H, J=1.2 Hz); $^{13}$C NMR (100 MHz; CDCl$_3$): δ 120.38, 132.03, 134.87, 136.90, 183.03.

Compound 12a: 3-bromothiophene-2-carbaldehyde (13a) (11 g, 57.6 mmol) was dissolved in methanol (300 ml) and cooled to 0° C. NaBH$_4$ (3.3 g, 86.4 mmol) was added in small portions to the mixture and stirred for 4 h. Water (100 mL) was added to the mixture and it was extracted with ether for three times. The organic phases were collected, dried over magnesium sulfate, filtered and concentrated under vacuum. The product was purified by column chromatography on silica gel with hexane/ethyl acetate (10:1) as eluent to give compound 12a as a colourless oil. Yield: 10.9 g (98%). $^1$H NMR (700 MHz, CDCl$_3$) δ 7.28 (d, 1H, J=5.2 Hz), 6.98 (d, 1H, J=5.2 Hz), 4.83 (d, 2H, J=6.4 Hz), 2.98 (s, br, 1H); $^{13}$C NMR (176 MHz, CDCl$_3$) δ 138.31, 130.13, 125.48, 108.89, 58.96.

Compound 11a: Imidazole (8.82 g, 129.5 mmol) was added to a solution of (3-bromothiophen-2-yl)methanol (12a) (10 g, 51.8 mmol) and triisopropylchlorosilane (11.98 g, 62.16 mmol) in dichloromethane. The mixture was stirred for 12 h, diluted with saturated aq. NH4Cl, extracted with EtOAc, washed with brine and concentrated in vacuo. The residue was purified by column chromatography on silica gel (eluent: Petroleum ether/ethyl acetate=50:1) to provide compound 11a as a colorless solid (17.74 g, 98% yield). $^1$HNMR (700 MHz, CDCl$_3$) δ 7.21 (d, J=5.3 Hz, 1H), 6.92 (d, J=5.3 Hz, 1H), 4.92 (s, 2H), 1.22-1.18 (m, 3H), 1.12 (s, 18H); $^{13}$CNMR (176 MHz, CDCl$_3$) δ 140.83, 129.60, 124.39, 105.30, 61.23, 18.01, 12.01.

Example 2

Preparation of Polymer P1 Comprising a Unit of Formula 1A

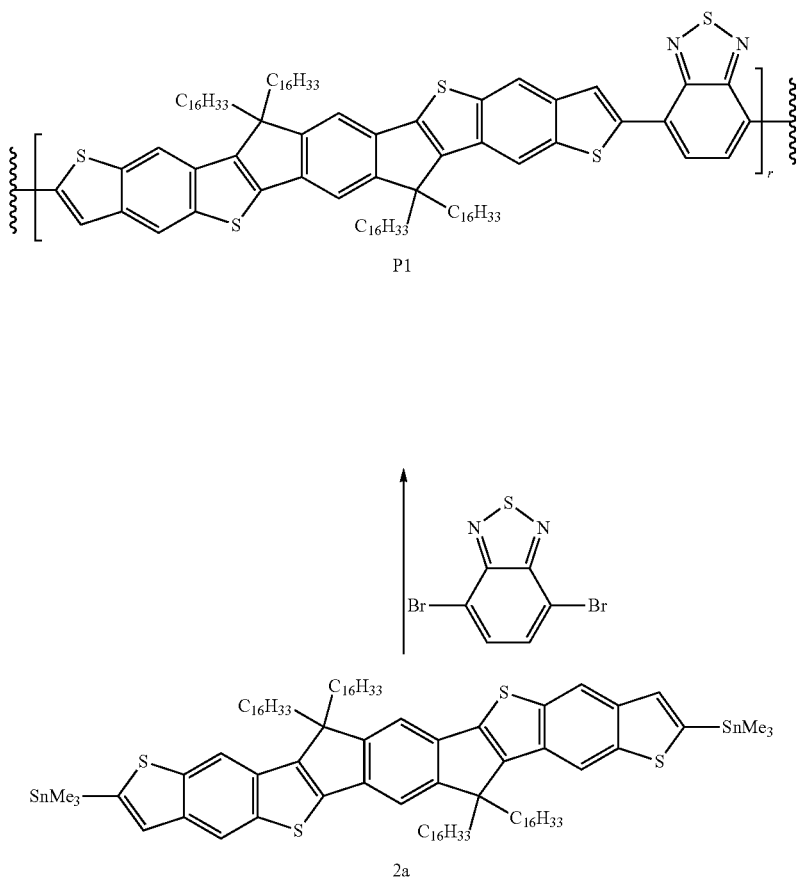

-continued
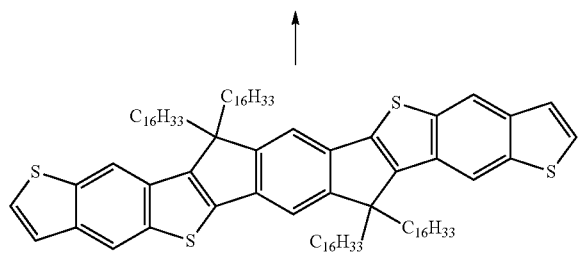
3a
↑
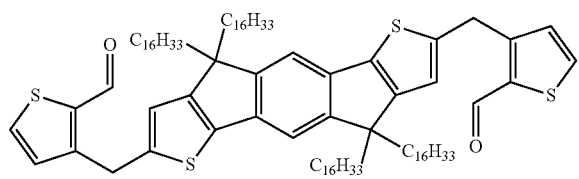
4a
↑
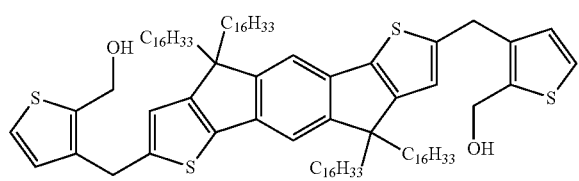
5a
↑
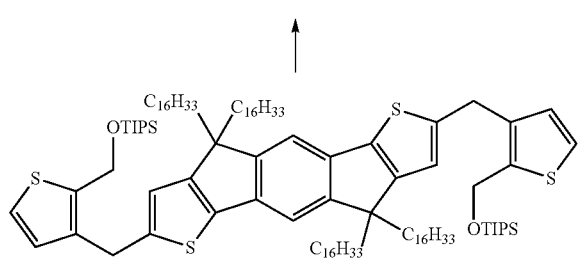
6a
↑
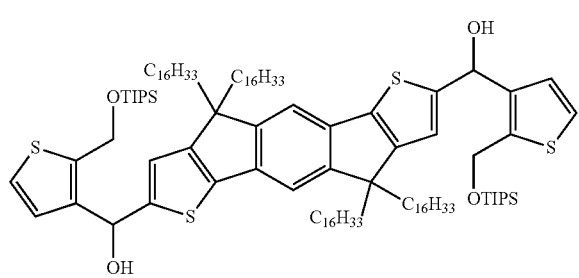
7a -continued

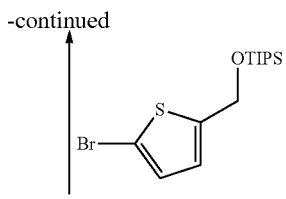

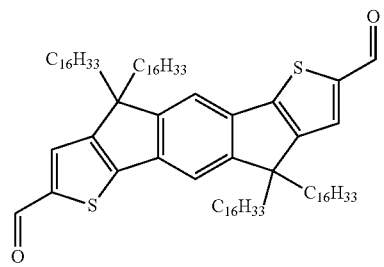

8a

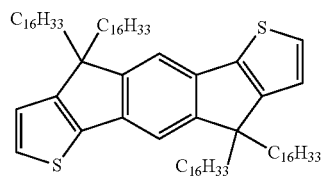

9a

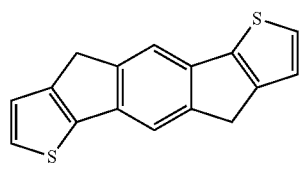

10a

Compound 10a and compound 9a were synthesized as described in W. Zhang, J. Smith, S. E. Watkins, R. Gysel, M. McGehee, A. Salleo, J. Kirkpatrick, S. Ashraf, T. Anthopoulos, M. Heeney, I. McCulloch, *J. Am. Chem. Soc.* 2010, 132, 11437.

Compound 8a: 4,4,9,9-tetrahexadecyl-4,9-dihydro-s-indaceno[1,2-b:5,6-b']dithiophene (9a) (10 g, 8.59 mmol) was dissolved in anhydrous THF (100 mL) and cooled down to −78' C under argon, n-butyllithium solution (2.5M, 8.59 mL) was added dropwise and the mixture was warmed up to 0° C. and stirred for 30 min. The mixture was cooled down to −78° C. again and then 1 mL of DMF was added dropwise into the solution and the mixture was warmed up to room temperature and stirred for another 6 hours. Water (100 mL) was added to the mixture and it was extracted with ethyl acetate for three times. The organic phases were collected, dried over magnesium sulfate, filtered and concentrated under vacuum. The product was purified by column chromatography on silica gel with hexane/ethyl acetate (5:1) as eluent to give compound 8a as a yellow solid (9.75 g, 93% yield). $^1$H NMR (500 MHz, CDCl$_3$) δ 9.94 (s, 1H), 7.66 (s, 1H), 7.48 (s, 1H), 2.12-2.10 (m, 8H), 1.36-0.92 (m, 104H), 0.91-0.87 (m, 12H), 0.82-0.65 (m, 8H); $^{13}$C NMR (126 MHz, CDCl$_3$) δ 182.96, 156.06, 155.18, 151.40, 145.60, 136.47, 130.41, 115.03, 53.81, 39.12, 32.11, 30.12, 29.84, 29.76, 29.43, 24.32, 22.81, 14.22.

Compound 7a: (3-bromothiophen-2-yl)methoxy)triisopropylsilane (11a) (5 g, 14.3 mmol), prepared as described in example 1, was dissolved in 100 mL anhydrous diethyl ether and cooled to −78° C., n-Butyllithium solution (2.5M, 5.72 mL) was added dropwise stirred for 30 min. 4,4,9,9-tetrahexadecyl-4,9-dihydro-s-indaceno[1,2-b:5,6-b']dithiophene-2,7-dicarbaldehyde (8a) (5.82 g, 4.76 mmol) dissolved in 50 mL diethyl ether was added dropwise into the solution and stirred for further 30 min. The mixture was warmed up to room temperature and stirred overnight. Water (150 mL) was added to the mixture and it was extracted with ethyl acetate for three times. The organic phases were collected, dried over magnesium sulfate, filtered and concentrated under vacuum. The product was purified by column chromatography on silica gel with hexane/dichloromethane (3:1) as eluent to give compound 7a as a brown liquid (6.04 g, 72% yield). $^1$H NMR (700 MHz, CDCl$_3$) δ 7.26 (s, 2H), 7.16 (s, 2H), 7.14 (d, J=5.2 Hz, 2H), 7.03 (d, J=5.2 Hz, 2H), 6.17 (d, J=4.8 Hz, 2H), 4.97 (s, 4H), 2.15-2.10 (m, 8H), 1.23-1.14 (m, 6H), 1.34-0.97 (m, 14OH), 0.91-0.82 (m, 12H), 0.81-0.65 (m, 8H); $^{13}$C NMR (176 MHz, CDCl$_3$) δ 171.19, 154.24, 152.54, 148.90, 145.69, 141.11, 140.71, 139.54, 135.67, 128.11, 126.40, 124.23, 123.09, 122.98, 119.11, 112.79, 60.43, 31.96, 29.76, 29.71, 29.41, 22.73, 21.08, 18.03, 18.01, 17.99, 17.73, 14.22, 14.16, 12.02, 11.95.

Compound 6a: Compound 7a (10.87 g, 6.17 mmol) was dissolved in 100 mL dichloromethane and then ZnI$_2$ (0.40 g, 1.24 mmol) was added in one portion, followed by the addition of NaBH$_3$CN (1.17 g, 18.52 mmol). The mixture was stirred overnight and then quenched by Water (100 mL). The mixture was extracted with ethyl acetate for three times. The organic phases were collected, dried over magnesium sulfate, filtered and concentrated under vacuum. The product was purified by column chromatography on silica gel with hexane as eluent to give compound 6a as a yellow liquid (10.04 g, 94% yield).

$^1$H NMR (700 MHz, CDCl$_3$) δ 7.26 (s, 2H), 7.14 (d, J=5.1 Hz, 2H), 6.87 (d, J=5.1 Hz, 2H), 6.65 (s, 2H), 4.96 (s, 4H), 4.14 (s, 4H), 2.15-2.10 (m, 8H), 1.28-1.14 (m, 6H), 1.34-0.96 (m, 140H), 0.91-0.85 (m, 12H), 0.82-0.64 (m, 8H); $^{13}$C NMR (176 MHz, CDCl$_3$) δ 154.43, 152.29, 145.05, 139.98, 139.90, 135.51, 134.85, 129.04, 126.84, 123.09, 121.23, 119.68, 112.50, 59.59, 41.36, 39.07, 36.09, 31.96, 29.75, 27.70, 24.24, 22.73, 20.48, 18.62, 17.85, 14.17, 12.97, 11.48.

Compound 5a: Compound 6a (5.58 g, 3.23 mmol) was dissolved in 100 mL THF and TBAF (1M in THF, 8.07 mL) was added into the solution and the mixture was stirred overnight and then quenched by Water (100 mL). The mixture was extracted with ethyl acetate for three times. The organic phases were collected, dried over magnesium sulfate, filtered and concentrated under vacuum. The product was purified by column chromatography on silica gel with hexane/dichloromethane (1:1) as eluent to give compound 5a as a yellow liquid (4.35 g, 95% yield). $^1$H NMR (700 MHz, CDCl$_3$) δ 7.26 (s, 2H), 7.21 (d, J=5.1 Hz, 2H), 6.93 (d, J=5.1 Hz, 2H), 6.69 (s, 2H), 4.83 (s, 4H), 4.21 (s, 4H), 2.14-2.12 (m, 8H), 1.32-0.97 (m, 104H), 0.91-0.84 (m, 12H), 0.82-0.64 (m, 8H); $^{13}$C NMR (176 MHz, CDCl$_3$) δ 171.26, 154.54, 152.31, 145.13, 140.06, 137.83, 137.71, 135.49, 129.52, 124.29, 119.71, 112.55, 60.46, 57.78, 53.94, 39.07, 31.96, 30.08, 29.75, 29.71, 29.69, 29.46, 29.41, 24.23, 22.73, 21.09, 17.73, 14.22, 14.17, 12.29.

Compound 4a: Compound 5a (5.22 g, 3.68 mmol) was dissolved in 100 mL dichloromethane and Dess-Martin periodinane (3.91 g, 9.22 mmol) was added into the solution and the mixture was stirred overnight and then slowly quenched by saturated NaHCO$_3$ solution. The mixture was stirred at room temperature for 30 min and then saturated NaS$_2$SO$_3$ solution was added. The mixture was extracted with ethyl acetate for three times. The organic phases were collected, dried over magnesium sulfate, filtered and concentrated under vacuum. The product was purified by column chromatography on silica gel with hexane/dichloromethane (1:1) as eluent to give compound 4a as a yellow solid (4.52 g, 87% yield). $^1$H NMR (700 MHz, CDCl$_3$) δ 10.13 (s, 2H), 7.65 (d, J=5.0 Hz, 2H), 7.14 (s, 2H), 7.05 (d, J=5.0 Hz, 2H), 6.74 (s, 2H), 4.56 (s, 4H), 2.13-2.11 (m, 8H), 1.36-0.96 (m, 104H), 0.90-0.86 (m, 12H), 0.83-0.69 (m, 8H); $^{13}$C NMR (176 MHz, CDCl$_3$) δ 182.09, 154.69, 152.44, 149.14, 143.00, 141.50, 140.61, 137.85, 135.50, 134.50, 131.27, 131.08, 128.42, 128.26, 53.93, 39.01, 31.90, 30.25, 29.71, 29.73, 29.63, 29.41, 29.49, 24.22, 22.71, 21.39, 17.43, 14.12, 14.10, 12.49.

Compound 3a: 3,3'-((4,4,9,9-tetrahexadecyl-4,9-dihydro-s-indaceno[1,2-b:5,6-b']dithiophene-2,7-diyl)bis(methylene))bis(thiophene-2-carbaldehyde) (4a) (3.77 g, 2.67 mmol) was dissolved in 100 mL toluene and 5 g Amberlyst-15 was added into the solution and the mixture was refluxed overnight and the water generated in situ was removed by a Dean-Stark Trap. The mixture was filtered, and the filtrate was concentrated under vacuum. The crude product was purified by column chromatography on silica gel with hexane as eluent to give compound 3a as a pale yellow solid (2.28 g, 62% yield). $^1$H NMR (700 MHz, CD$_2$Cl$_2$) δ 8.37 (s, 2H), 8.31 (s, 2H), 7.52 (s, 2H), 7.51 (d, J=5.3 Hz, 2H), 7.41 (d, J=5.4 Hz, 2H), 2.13-2.11 (m, 8H), 1.34-0.96 (m, 104H), 0.91-0.86 (m, 12H), 0.82-0.69 (m, 8H); $^{13}$C NMR (176 MHz, CD$_2$Cl$_2$). 13C NMR (176 MHz, CDCl3) δ 139.07, 131.37, 127.83, 126.75, 122.52, 122.09, 121.64, 117.43, 111.44, 108.12, 103.46, 99.16, 98.40, 40.43, 24.10, 16.91, 14.67, 14.65, 14.64, 14.61, 14.58, 14.46, 14.35, 14.17, 8.78, 7.68, 0.90.

Compound 2a: Compound 3a (3.42 g, 2.49 mmol) was dissolved in 80 mL THF and cooled to −78° C., n-butyl-lithium solution (2.5M, 2.49 mL) was added dropwise stirred for 30 min. 6.23 mL Me$_3$SnCl solution (1M in THF) was added dropwise into the solution and the mixture was warmed up to room temperature and stirred overnight and then quenched by water (80 mL). The mixture was extracted with ethyl acetate for three times. The organic phases were collected, concentrated under vacuum. The product was recrystallized in acetonitrile/dichloromethane to afford compound 2a as a pale yellow solid. (4.02 g, 95% yield). $^1$H NMR (500 MHz, CD$_2$Cl$_2$) δ 8.36 (s, 1H), 8.32 (s, 2H), 7.53 (s, 2H), 7.50 (s, 2H), 2.53-2.34 (m, 4H), 2.34-2.16 (m, 4H), 1.41-0.95 (m, 104H), 0.93-0.86 (m, 12H), 0.84-0.61 (m, 8H) 0.50 (s, 18H).

Polymer P1: A 2.5 mL microwave vial was charged with compound 2a (0.40 g, 0.233 mmol), 4,7-dibromobenzo[c][1,2,5]thiadiazole (0.068 g, 0.233 mmol), 2 mol % of tris(dibenzylideneacetone)dipalladium (2.9 mg, 0.005 mmol) and tri(o-tolyl) phosphine (6 mg, 0.02 mmol). The vial was sealed and chlorobenzene (1 mL) was added. The obtained solution was degassed with argon for 30 minutes. The vial was subjected to the following reaction conditions in the microwave reactor: 2 minutes at 100° C., 2 minutes at 120° C., 5 minutes at 140° C., 5 minutes at 160° C. and 20 minutes at 180° C. The polymer was endcapped by addition of 0.1 eq. of 2-bromobenzene before the reaction mixture was resubmitted to the microwave reactor, 1 minute at 100° C., 1 minute at 120° C., 2 minutes at 140° C. and 5 minutes at 160° C. The polymeric solution was cooled down and 0.1 eq. of 2-(trimethylstannyl)benzene was added by syringe. The reaction vial was subjected to the previously mentioned temperature scheme to finalize the end-capping reaction. After reaction, the crude polymer was precipitated in methanol and then further purified by Soxhlet extractions with acetone, hexane and chloroform for 24 hours each. Remaining palladium residues were removed by treating a polymeric chloroform solution with an aqueous sodium diethyldithiocarbamate solution for 2 hours at 50° C. under vigorous stirring. Afterwards the organic phase was separated from the aqueous phase and washed several times with water. The polymeric solution was concentrated under reduced pressure and precipitated into cold methanol. Polymer P1 was filtered off and dried under high vacuum for at least 24 hours. $^1$H NMR (500 MHz, CDCl$_3$) δ 8.71 (br, 2H), 8.37 (br, 2H), 8.13 (br, 2H), 7.68 (br, 2H), 7.74 (br, 2H), 2.14-2.10 (br, 8H), 0.95-1.32 (br, 104H), 0.91-0.84 (br, 12H), 0.82-0.61 (br, 8H).

Example 3

Preparation of a Bottom-Contact, Top-Gate Organic Fieldeffect Transistor (OFET) Comprising Polymer P1 as Semiconducting Material Gold source and drain contacts were evaporated on glass, followed by treatment with pentafluorobenzenethiol. The semiconducting layer was then spin-coated from 10 mg mL$^{-1}$ solution of polymer P1 in chlorobenzene and Cytop®, a commercially available fluoropolymer, was deposited as gate dielectric. An Ag gate electrode was used. The channel width and length are W=1000 μm and L=30 μm.

The transfer and output characteristics of the OFET were measured.

FIGS. 1 and 2 show the transfer and output characteristics of the OFET.

Field effect mobility was calculated using the standard thin film transistor model in the saturation regime of the device using:

$$\mu_{sat} = \frac{2L}{WC} \cdot \left(\frac{\partial I_{dsat}}{\partial V_g}\right)^2,$$

where L, W, and C are the channel length, channel width, and capacitance of the dielectric, respectively.

The average saturation hole mobility of the OFET was 2.5 cm$^2$ V$^{-1}$ s$^{-1}$, with an on/off ratio of 2×10$^5$ and approximately −17 V threshold voltage.

The invention claimed is:

1. Compounds comprising at least one unit of formula

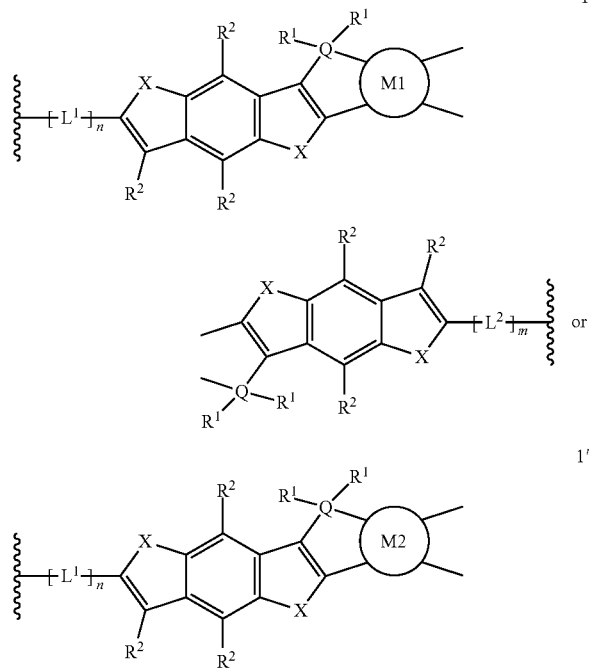

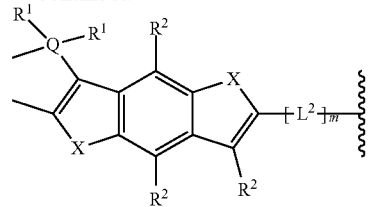

wherein
M1 and M2 are independently of each other an aromatic or heteroaromatic monocyclic or bicyclic ring system;
X is at each occurrence O, S, Se or Te,
Q is at each occurrence C, Si or Ge,
R$^1$ is at each occurrence selected from the group consisting of H, C$_{1-50}$-alkyl, —[CH$_2$]$_o$—[O—SiR$^a$R$^a$]$_p$—OSiR$^a$R$^a$R$^a$, —[CH$_2$]$_o$—[R$^a$R$^a$Si—O]$_p$—SiR$^a$R$^a$R$^a$, —[CR$^b$R$^b$]$_q$—CR$^b$R$^b$R$^b$, C$_{2-50}$-alkenyl, C$_{2-50}$-alkynyl, C$_{5-8}$-cycloalkyl, C$_{6-14}$-aryl and 5 to 14 membered heteroaryl,
wherein
is an integer from 0 to 10,
p is an integer from 1 to 40,
R$^a$ is at each occurrence C$_{1-10}$-alkyl, C$_{2-10}$-alkenyl or C$_{2-10}$-alkynyl,
q is an integer from 1 to 50,
R$^b$ is at each occurrence H or halogen, with the proviso that not all R$^b$ in —[CR$^b$R$^b$]$_q$—CR$^b$R$^b$R$^b$ are H,
C$_{1-50}$-alkyl, C$_{2-50}$-alkenyl and C$_{2-50}$-alkynyl can be substituted with one to four substituents independently selected from the group consisting of OR$^c$, OC(O)—R$^c$, C(O)—OR$^c$, C(O)—R$^c$, NR$^c$R$^c$, NR$^c$—C(O)R$^c$, C(O)—NR$^c$R$^c$, N[C(O)R$^c$][C(O)R$^c$], SR$^c$, CN, —SiR$^c$R$^c$R$^c$ and NO$_2$,
C$_{5-8}$-cycloalkyl can be substituted with one or two substituents independently selected from the group consisting of C$_{1-10}$-alkyl, C$_{2-10}$-alkenyl, C$_{2-10}$-alkynyl, OR$^c$, OC(O)—R$^c$, C(O)—OR$^c$, C(O)—R$^c$, NR$^c$R$^c$, NR$^c$—C(O)R$^c$, C(O)—NR$^c$R$^c$, N[C(O)R$^c$][C(O)R$^c$], SR$^c$, halogen, CN, —SiR$^c$R$^c$R$^c$ and NO$_2$; and one CH$_2$-group of C$_{5-8}$-cycloalkyl can be replaced by O, S, OC(O), CO, NR$^c$ or NR$^c$—CO,
C$_{6-14}$-aryl and 5 to 14 membered heteroaryl can be substituted with one to three substituents independently selected from the group consisting of C$_{1-10}$-alkyl, C$_{2-10}$-alkenyl, C$_{2-10}$-alkynyl, OR$^c$, OC(O)—R$^c$, C(O)—OR$^c$, C(O)—R$^c$, NR$^c$R$^c$NR$^c$—C(O)R$^c$, C(O)—NR$^c$R$^c$, N[C(O)R$^c$][C(O)R$^c$], SR$^c$, halogen, CN, and NO$_2$,
wherein
R$^c$ is at each occurrence H, C$_{1-20}$-alkyl, C$_{2-10}$-alkenyl or C$_{2-10}$-alkynyl,
R$^2$ is at each occurrence H, C$_{1-30}$-alkyl, C$_{2-30}$-alkenyl or C$_{2-30}$-alkynyl or halogen,
n is 0, 1, 2, 3 or 4,
m is 0, 1, 2, 3 or 4,
and
L$^1$ and L$^2$ are independently from each other and at each occurrence selected from the group consisting of C$_{6-26}$-arylene, 5 to 20 membered heteroarylene,

and

-continued

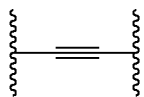

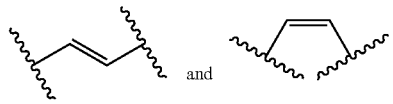

wherein

C$_{6-26}$-arylene and 5 to 20 membered heteroarylene can be substituted with one to four substituents R$^d$ at each occurrence selected from the group consisting of H, C$_{1-30}$-alkyl, C$_{2-30}$-alkenyl, C$_{2-30}$-alkynyl and halogen, and and can be substituted with one or two substituents at each occurrence selected from the group consisting of R$^e$, COOR$^e$ and CN, wherein R$^e$ is at each occurrence selected from the group consisting of H, C$_{1-30}$-alkyl, C$_{2-30}$-alkenyl and C$_{2-30}$-alkynyl.

2. The compounds of claim 1 comprising at least one unit of formula

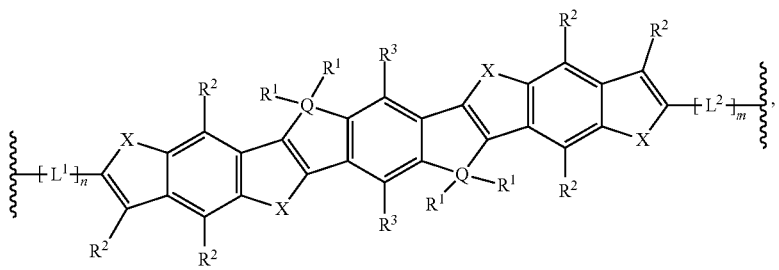

1A

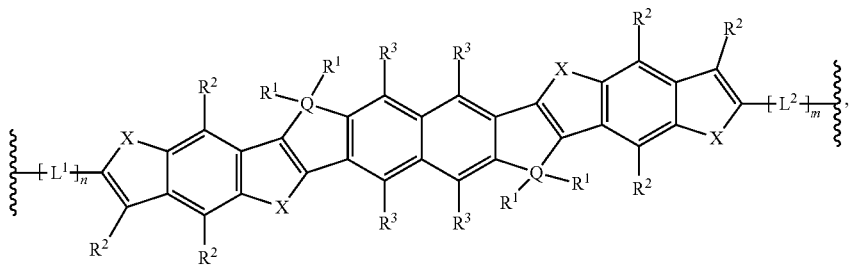

1B

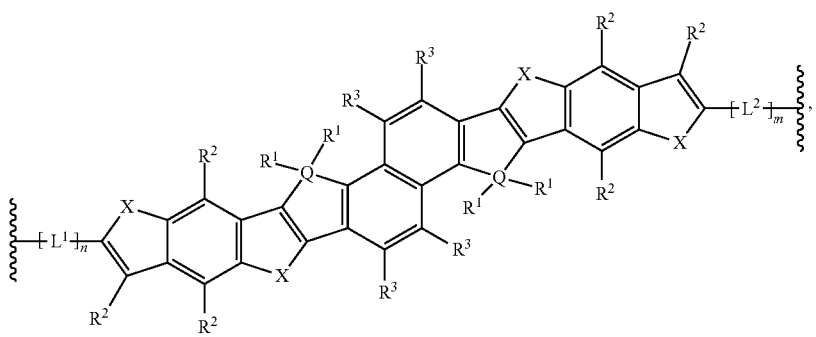

1C

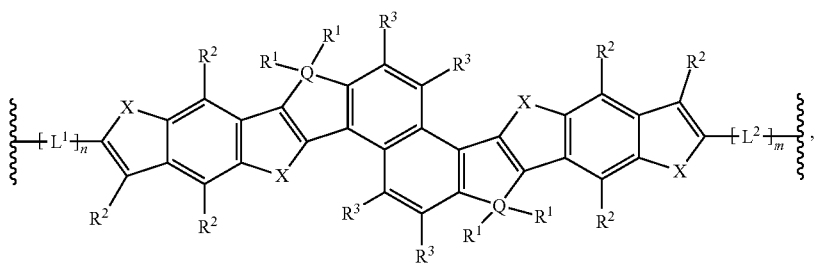

1D

-continued

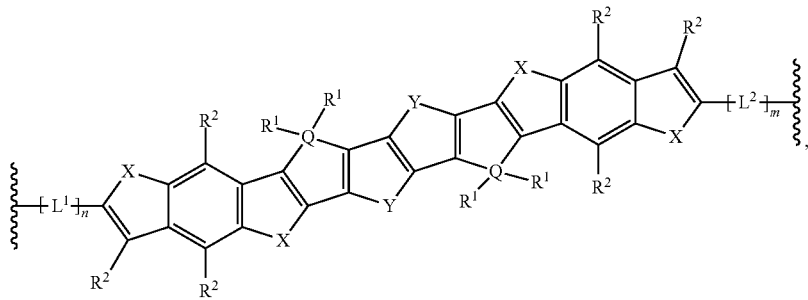
1E

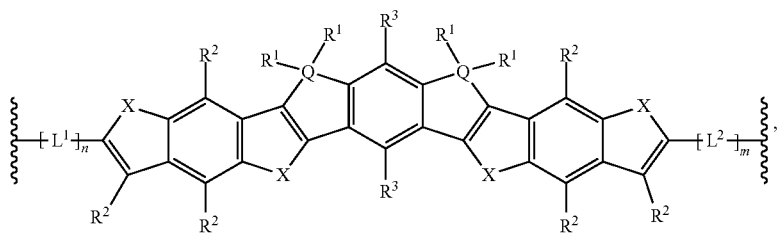
1'A

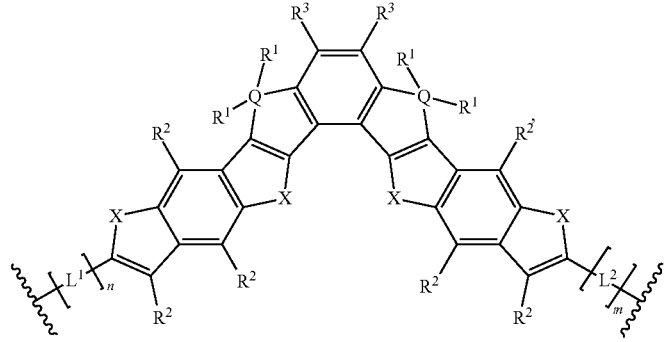
1'B

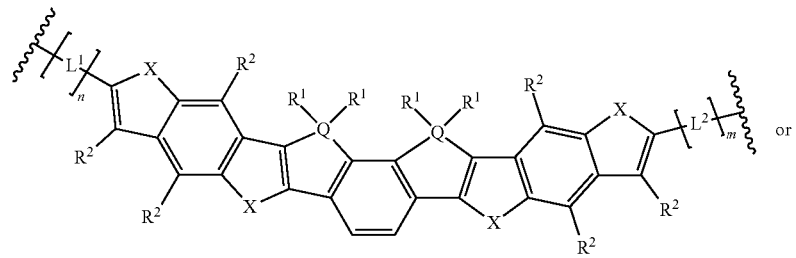
1'C

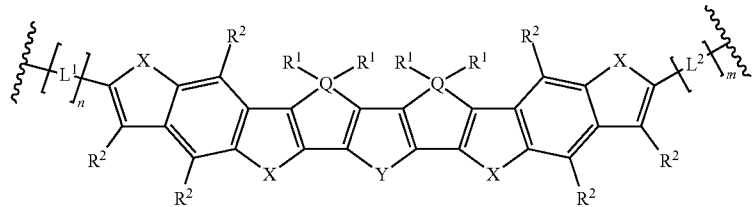
1'D wherein
X, Q, R¹, R², L¹, L², n and m are as defined in claim 1,
Y is at each occurrence O, S, Se or Te, and
R³ is at each occurrence H, $C_{1-30}$-alkyl, $C_{2-30}$-alkenyl or $C_{2-30}$-alkynyl or halogen.

3. The compounds of claim 1, wherein the compound is a polymer.

4. The compounds of claim 1, wherein X is O, S or Se.

5. The compounds of claim 1, wherein Q is C or Si.

6. The compounds of claim 1, wherein R¹ is at each occurrence selected from the group consisting of H, $C_{1-50}$-alkyl, —[CH$_2$]$_o$—[R$^a$R$^a$Si—O]$_p$—SiR$^a$R$^a$R$^a$, —[CR$^b$R$^b$]$_q$CR$^b$R$^b$, $C_{2-50}$-alkenyl and $C_{2-50}$-alkynyl,
wherein
o is an integer from 1 to 10,
p is an integer from 1 to 40,
R$^a$ is at each occurrence $C_{1-10}$-alkyl, $C_{2-10}$-alkenyl or $C_{2-10}$-alkynyl, q is an integer from 1 to 50, $R^b$ is at each occurrence H or halogen, with the provisio that not all $R^b$ in —$[CR^bR^b]_q$—$CR^bR^bR^b$ are H, $C_{1-50}$-alkyl, $C_{2-50}$-alkenyl and $C_{2-50}$-alkynyl can be substituted with one to four substituents independently selected from the group consisting of $OR^c$, $OC(O)$—$R^c$, $C(O)$—$OR^c$, $C(O)$—$R^c$, $NR^cR^cNR^c$—$C(O)R^c$, $C(O)$—$NR^cR^c$, $N[C(O)R^c][C(O)R^c]$, $SR^c$, CN, and $NO_2$, wherein $R^c$ is at each occurrence H, $C_{1-20}$-alkyl, $C_{2-10}$-alkenyl or $C_{2-10}$-alkynyl.

7. The compounds of claim 1, wherein $R^1$ is at each occurrence $C_{1-50}$-alkyl.

8. The compounds of claim 1, wherein $R^2$ is at each occurrence H, $C_{1-30}$-alkyl or halogen.

9. The compounds of claim 1, wherein m is 0, 1 or 2.

10. The compounds of claim 1, wherein n is 0.

11. The compounds of claim 1, wherein $L^1$ and $L^2$ are independently from each other and at each occurrence selected from the group consisting of $C_{6-26}$-arylene, 5 to 20 membered heteroarylene, and

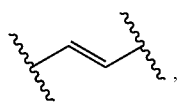 [SMILES: */C=C/*]

wherein $C_{6-26}$-arylene and 5 to 20 membered heteroarylene can be substituted with one to four substituents $R^d$ at each occurrence selected from the group consisting of $C_{1-30}$-alkyl, $C_{2-30}$-alkenyl, $C_{2-30}$-alkynyl and halogen, wherein $C_{6-26}$-arylene, optionally substituted with one to four substituents $R^d$, is selected from the group consisting of

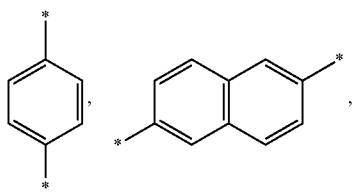

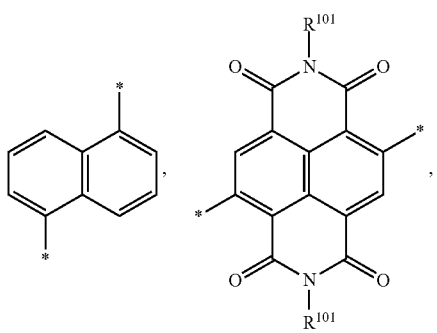

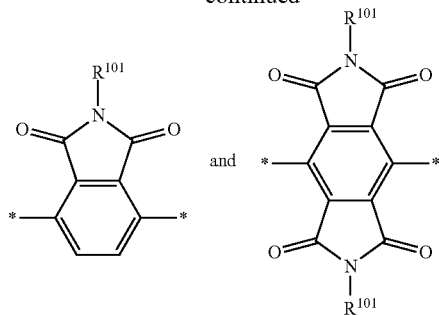

wherein $R^{101}$ is at each occurrence H or $C_{1-30}$-alkyl, and wherein 5 to 20 membered heteroarylene, optionally substituted with one to four substitutents $R^d$, are selected from the group consisting of

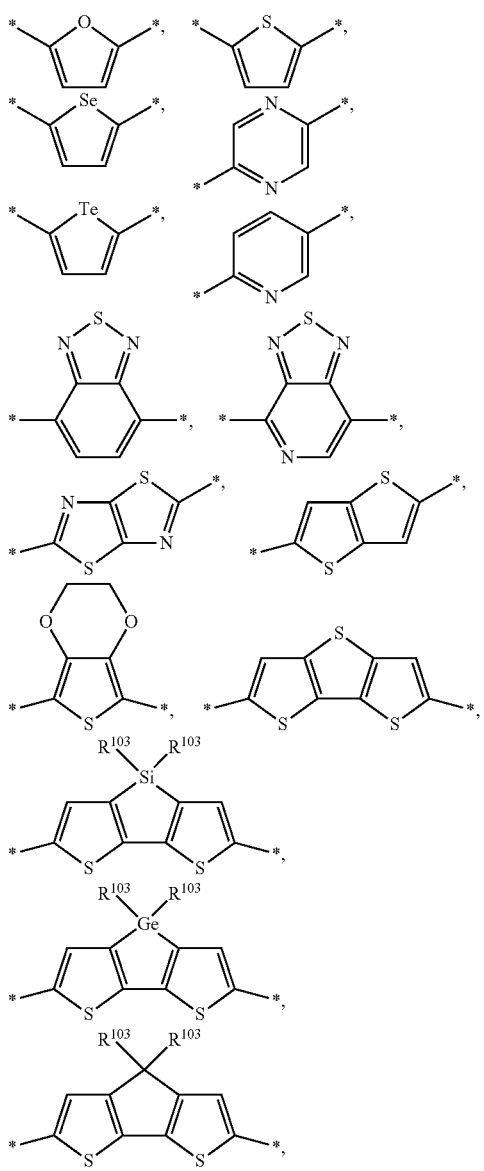

-continued
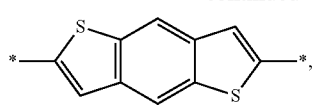
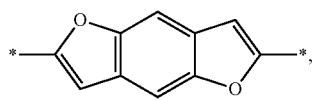
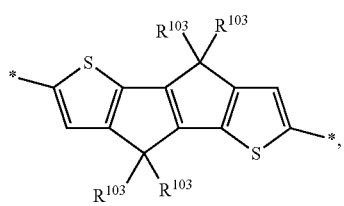
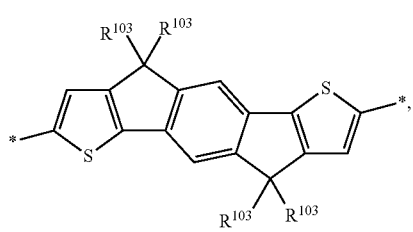
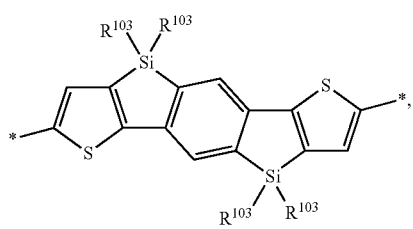
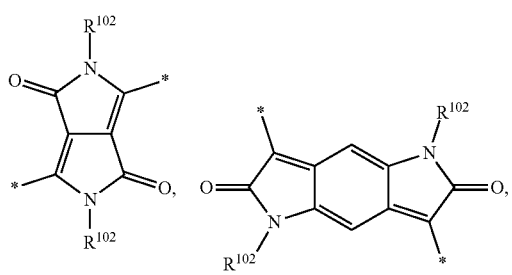
-continued
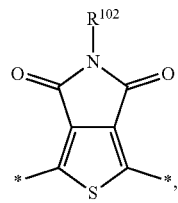
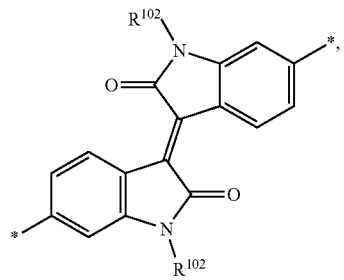
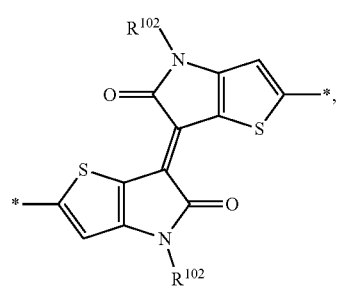
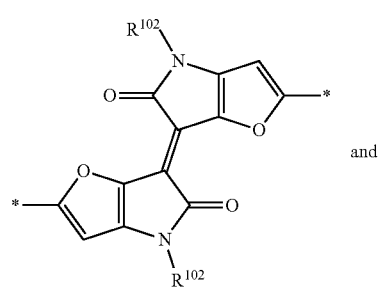
and
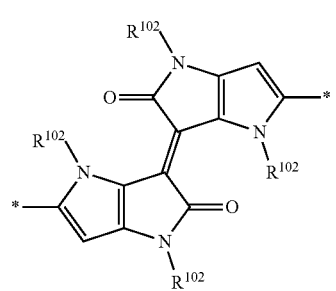
wherein
$R^{103}$ is at each occurrence H, $C_{1\text{-}30}$-alkyl, $C_{2\text{-}30}$-alkenyl or $C_{2\text{-}30}$-alkynyl or halogen,
$R^{102}$ is at each occurrence H or $C_{1\text{-}30}$-alkyl.
12. A process for the preparation of the compounds of claim 1 comprising at least one unit of formula

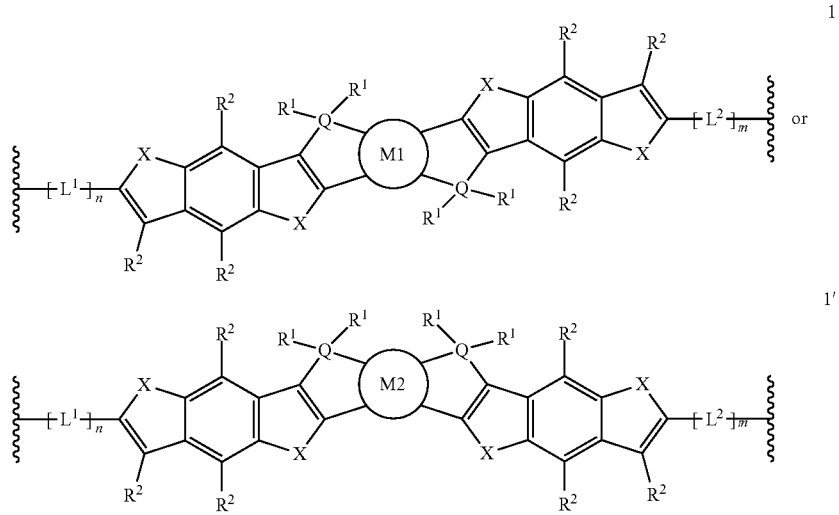

wherein
M1 and M2 are independently of each other an aromatic or heteroaromatic monocyclic or bicyclic ring system;
X is at each occurrence O, S, Se or Te,
Q is at each occurrence C, Si or Ge,
$R^1$ is at each occurrence selected from the group consisting of H, $C_{1-50}$-alkyl, —[$CH_2$]$_o$—[O—Si$R^a R^a$]$_p$—OSi$R^a R^a R^a$, —[$CH_2$]$_o$—[$R^a R^a$Si—O]$_p$—Si$R^a R^a R^a$, —[$CR^b R^b$]$_q$—$CR^b R^b R^b$, $C_{2-50}$-alkenyl, $C_{2-50}$-alkynyl, $C_{5-8}$-cycloalkyl, $C_{6-14}$-aryl and 5 to 14 membered heteroaryl,
wherein
o is an integer from 0 to 10,
p is an integer from 1 to 40,
$R^a$ is at each occurrence $C_{1-10}$-alkyl, $C_{2-10}$-alkenyl or $C_{2-10}$-alkynyl,
q is an integer from 1 to 50,
$R^b$ is at each occurrence H or halogen, with the provisio that not all $R^b$ in —[$CR^b R^b$]$_q$—$CR^b R^b R^b$ are H,
$C_{1-50}$-alkyl, $C_{2-50}$-alkenyl and $C_{2-50}$-alkynyl can be substituted with one to four substituents independently selected from the group consisting of $OR^c$, $OC(O)$—$R^c$, $C(O)$—$OR^c$, $C(O)$—$R^c$, $NR^c R^c$, $NR^c$—$C(O)R^c$, $C(O)$—$NR^c R^c$, $N[C(O)R^c][C(O)R]$, $SR^c$, CN, —Si$R^c R^c R^c$ and $NO_2$,
$C_{5-8}$-cycloalkyl can be substituted with one or two substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^c R^c$, $NR^c$—$C(O)R^c$, $C(O)$—$NR^c R^c$, $N[C(O)R^c][C(O)R]$, $SR^c$, halogen, CN, —Si$R^c R^c R^c$ and $NO_2$; and one $CH_2$-group of $C_{5-8}$-cycloalkyl can be replaced by O, S, OC(O), CO, $NR^c$ or $NR^c$—CO,
$C_{6-14}$-aryl and 5 to 14 membered heteroaryl can be substituted with one to three substituents independently selected from the group consisting of $C_{1-10}$-alkyl, $C_{2-10}$-alkenyl, $C_{2-10}$-alkynyl, $OR^c$, $OC(O)$—$R^c$, $C(O)$—$OR^c$, $C(O)$—$R^c$, $NR^c R^c$, $NR^c$—$C(O)R^c$, $C(O)$—$NR^c R^c$, $N[C(O)R^c][C(O)R^c]$, $SR^c$, halogen, CN, and $NO_2$,
wherein
$R^c$ is at each occurrence H, $C_{1-20}$-alkyl, $C_{2-10}$-alkenyl or $C_{2-10}$-alkynyl, $R^2$ is at each occurrence H, $C_{1-30}$-alkyl, $C_{2-30}$-alkenyl or $C_{2-30}$-alkynyl or halogen,
n is 0, 1, 2, 3 or 4,
m is 0, 1, 2, 3 or 4,
and
$L^1$ and $L^2$ are independently from each other and at each occurrence selected from the group consisting of $C_{6-26}$-arylene, 5 to 20 membered heteroarylene,

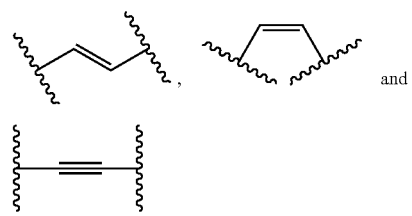
and wherein
$C_{6-26}$-arylene and 5 to 20 membered heteroarylene can be substituted with one to four substituents $R^d$ at each occurrence selected from the group consisting of H, $C_{1-30}$-alkyl, $C_{2-30}$-alkenyl, $C_{2-30}$-alkynyl and halogen, and

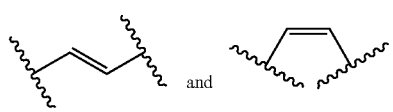
and and can be substituted with one or two substituents at each occurrence selected from the group consisting of $R^e$, $COOR^e$ and CN, wherein $R^e$ is at each occurrence selected from the group consisting of H, $C_{1-30}$-alkyl, $C_{2-30}$-alkenyl and $C_{2-30}$-alkynyl, which process comprises the step of treating a compound of formula

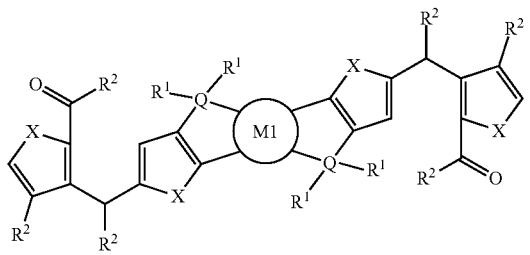

or

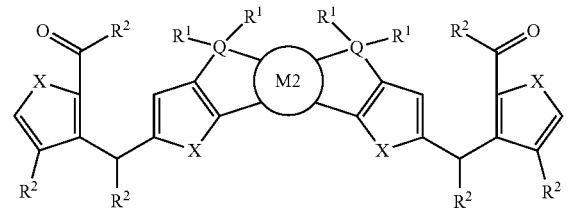

wherein M1, M2, X, Q, R¹ and R² are as defined for units of formula 1 and 1', with acid to afford a compound of formula

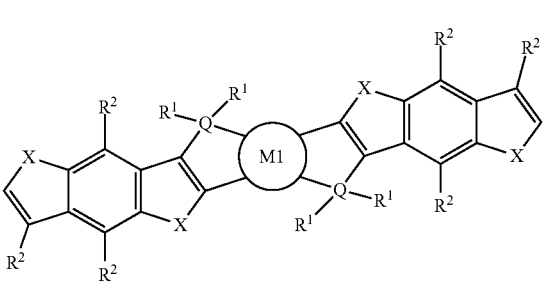

or

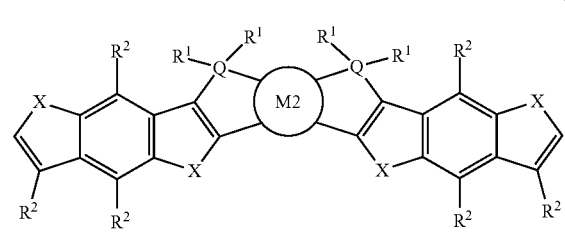

wherein M1, M2, X, Q, R¹ and R² are as defined for the units of formula 1 and 1'.

13. Compounds of formula

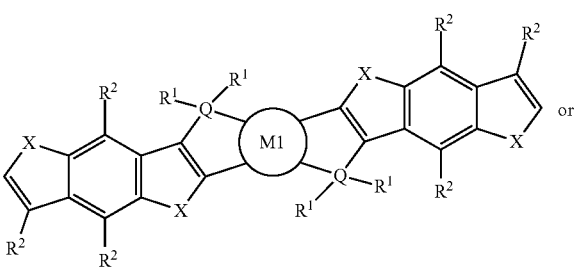

or

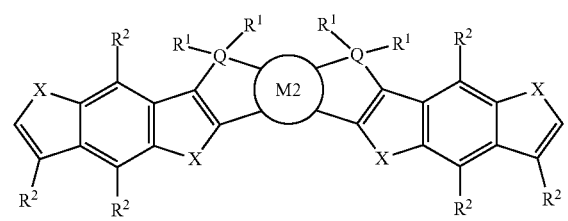

wherein

M1 and M2 are independently of each other an aromatic or heteroaromatic monocyclic or bicyclic ring system;

X is at each occurrence O, S, Se or Te,

Q is at each occurrence C, Si or Ge, $R^1$ is at each occurrence selected from the group consisting of H, $C_{1-50}$-alkyl, $-[CH_2]_o-[O-SiR^aR^a]_p-OSiR^aR^aR^a$, $-[CH_2]_o-[R^aR^aSi-O]_p-SiR^aR^aR^a$, $-[CR^bR^b]_q-CR^bR^bR^b$, $C_{2-50}$-alkenyl, $C_{2-50}$-alkynyl, $C_{5-8}$-cycloalkyl, $C_{6-14}$-aryl and 5 to 14 membered heteroaryl, wherein is an integer from 0 to 10, p is an integer from 1 to 40, $R^a$ is at each occurrence $C_{1-10}$-alkyl, $C_{2-10}$-alkenyl or $C_{2-10}$-alkynyl, q is an integer from 1 to 50, $R^b$ is at each occurrence H or halogen, with the proviso that not all $R^b$ in $-[CR^bR^b]_q-CR^bR^bR^b$ are H, $C_{1-50}$-alkyl, $C_{2-50}$-alkenyl and $C_{2-50}$-alkynyl can be substituted with one to four substituents independently selected from the group consisting of $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R^c]$, $SR^c$, CN, $-SiR^cR^cR^c$ and $NO_2$, $C_{5-8}$-cycloalkyl can be substituted with one or two substituents independently selected from the group consisting of $C_{1-10}$-alkyl, $C_{2-10}$-alkenyl, $C_{2-10}$-alkynyl, $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R]$, $SR^c$, halogen, CN, $-SiR^cR^cR^c$ and $NO_2$; and one $CH_2$-group of $C_{5-8}$-cycloalkyl can be replaced by O, S, OC(O), CO, $NR^c$ or $NR^c-CO$, $C_{6-14}$-aryl and 5 to 14 membered heteroaryl can be substituted with one to three substituents independently selected from the group consisting of $C_{1-10}$-alkyl, $C_{2-10}$-alkenyl, $C_{2-10}$-alkynyl, $OR^c$, $OC(O)-R^c$, $C(O)-OR^c$, $C(O)-R^c$, $NR^cR^c$, $NR^c-C(O)R^c$, $C(O)-NR^cR^c$, $N[C(O)R^c][C(O)R^c]$, $SR^c$, halogen, CN, and $NO_2$, wherein
R$^c$ is at each occurrence H, C$_{1-20}$-alkyl, C$_{2-10}$-alkenyl or C$_{2-10}$-alkynyl,
R$^2$ is at each occurrence H, C$_{1-30}$-alkyl, C$_{2-30}$-alkenyl or C$_{2-30}$-alkynyl or halogen.

14. Compounds of claim 13 which are of formula

3A
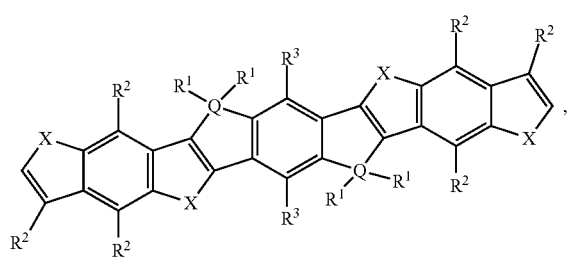

3B
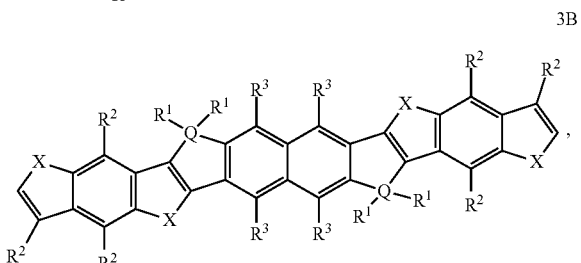

3C
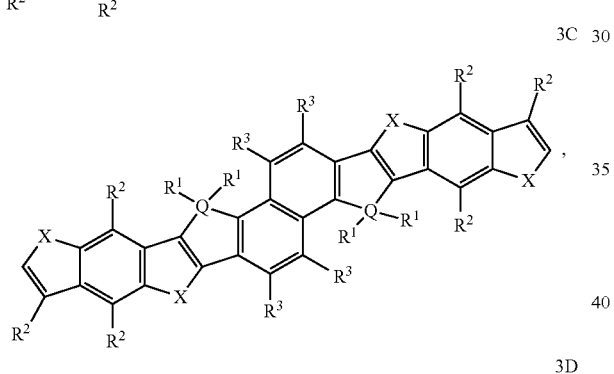

3D
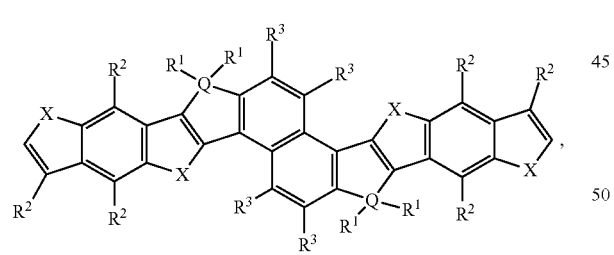

3E
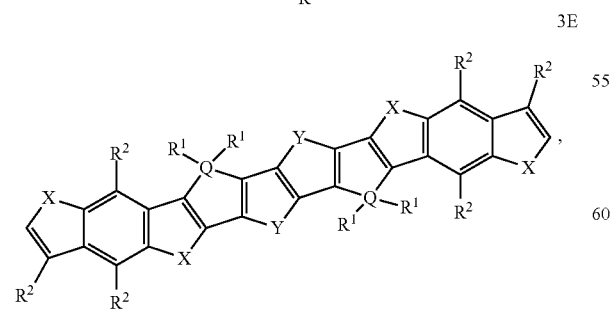

3'A
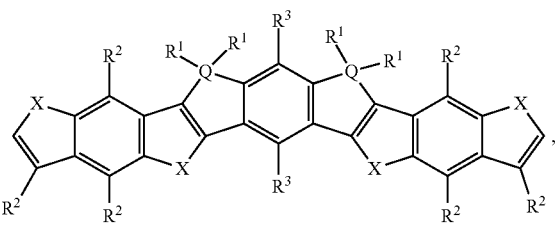

3'B
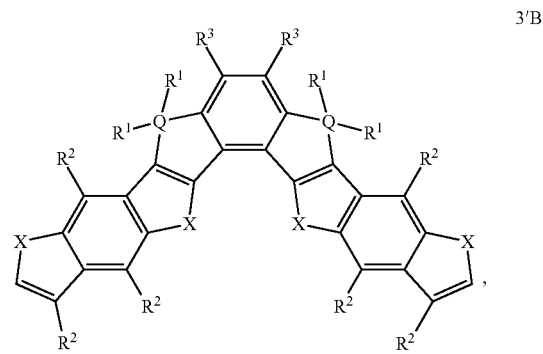

3'C
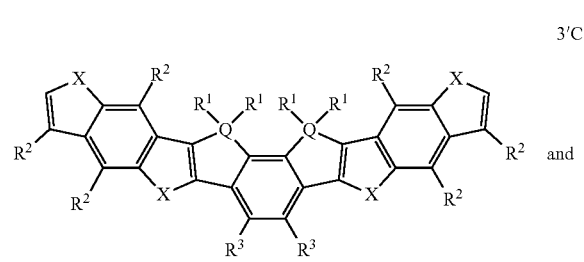

and

3'D
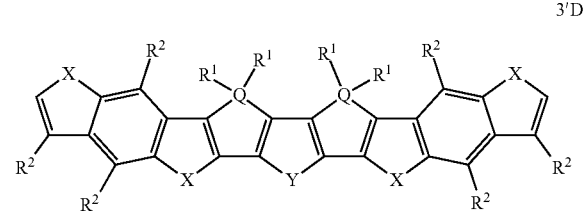

wherein
X, Q, R$^1$ and R$^2$ are as defined in claim 13, and
Y is at each occurrence O, S, Se or Te, and
R$^3$ is at each occurrence H, C$_{1-30}$-alkyl, C$_{2-30}$-alkenyl or C$_{2-30}$-alkynyl or halogen.

* * * * *